United States Patent
Anand et al.

(12)

(10) Patent No.: US 6,342,490 B1
(45) Date of Patent: Jan. 29, 2002

(54) PHARMACEUTICAL COMPOSITION CONTAINING USCHARIDIN OR ITS ANALOGUES

(75) Inventors: Chaman Lal Anand; William Howard Stimson; Alexander Irvine Gray, all of Glasgow (GB)

(73) Assignee: Phyto Corporation Limited, London (GB)

( * ) Notice: Subject to any disclaimer, the term of this patent is extended or adjusted under 35 U.S.C. 154(b) by 0 days.

(21) Appl. No.: 09/423,358

(22) PCT Filed: May 26, 1998

(86) PCT No.: PCT/GB98/01522

§ 371 Date: Jan. 5, 2000

§ 102(e) Date: Jan. 5, 2000

(87) PCT Pub. No.: WO98/52562

PCT Pub. Date: Nov. 26, 1998

(30) Foreign Application Priority Data

May 24, 1997 (GB) .............................. 9710698

(51) Int. Cl.[7] ........................ A61K 31/58; A61K 31/425
(52) U.S. Cl. ....................... 514/172; 514/365
(58) Field of Search ................... 514/365, 172

(56) References Cited

FOREIGN PATENT DOCUMENTS

WO          92/09295        6/1992

OTHER PUBLICATIONS

Hussein et al., J. Chem. Ecol., 20(1), 135–40 Abstract Only 1994.*

Parsons et al., "Cat assay for the emetic action of digitalis and related glycosides", Br. J. Pharmacol., vol. 42, No. 1, 1971, pp. 143–152.

Kiuchi et al., "Cytotoxic Principles of a Bangladeshi Crude Drug, Akond Mul (Roots of Calotropis gigantea L.)", Chem. Pharm. Bull., vol. 46, No. 3, 1998, pp. 528–530.

Mutlib et al., "In Vivo and In Vitro Metabolism of Gomphoside, a Cardiotonic Steroid with Doubly–Linked Sugar", J. Steroid Biochem., vol. 28, No. 1, 1987, pp. 65–76.

* cited by examiner

*Primary Examiner*—Jerome D. Goldberg
(74) *Attorney, Agent, or Firm*—Ratner & Prestia

(57) ABSTRACT

The invention provides compositions comprising uscharin and the use of uscharin to combat cell proliferation for example in the treatment of cancer. Administration of uscharin may kill or reduce the growth rate of cancer cells and may also be of application in other medical conditions presenting symptoms of excessive or uncontrolled cell proliferation. The composition may be administered by any convenient route and formulated accordingly. The composition may be administered locally or generally and may be suitably dissolved and/or suspended in a pharmaceutically acceptable liquid carrier medium.

2 Claims, 41 Drawing Sheets

Log10 Concentration

Figure 1F:
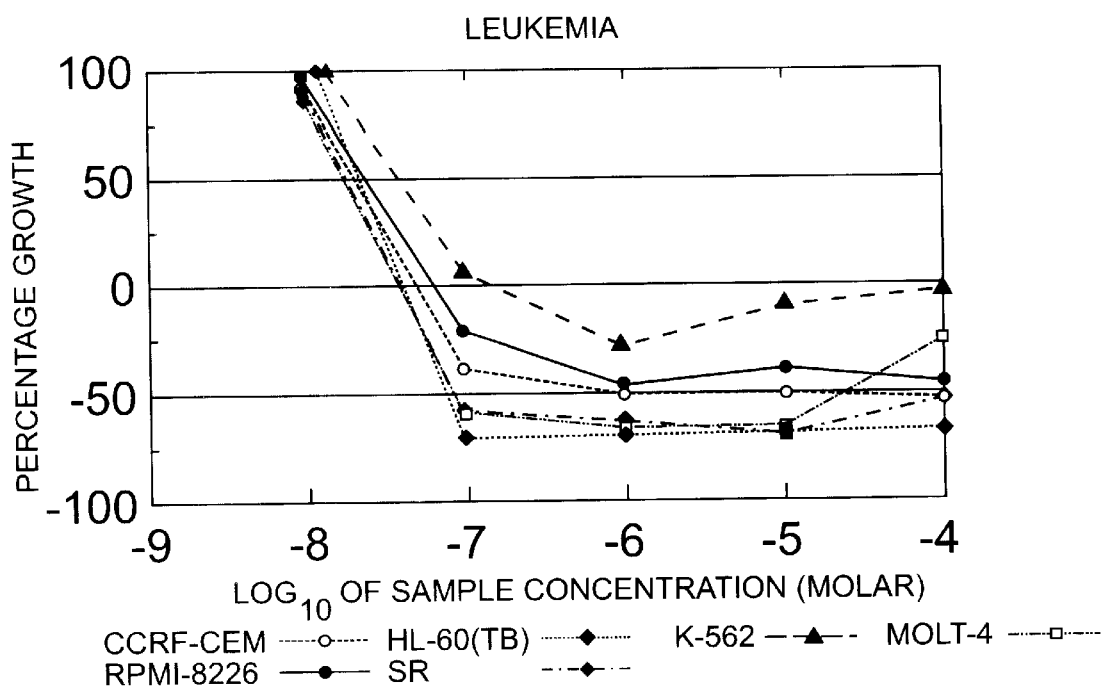
Figure 1G:
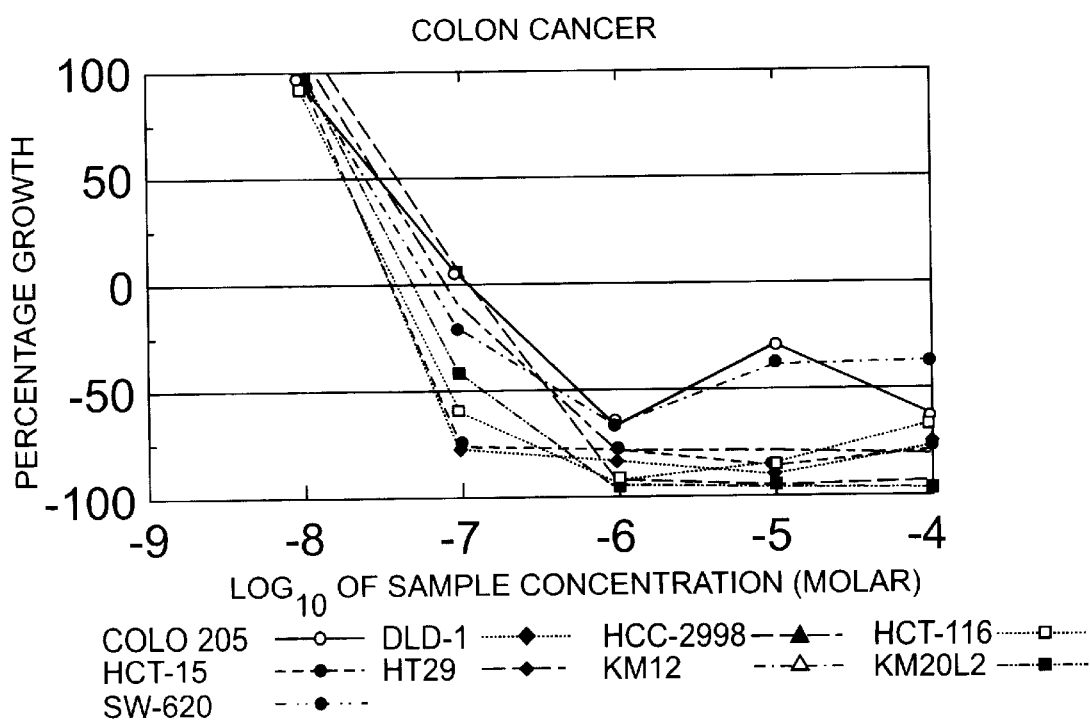
Figure 1H:
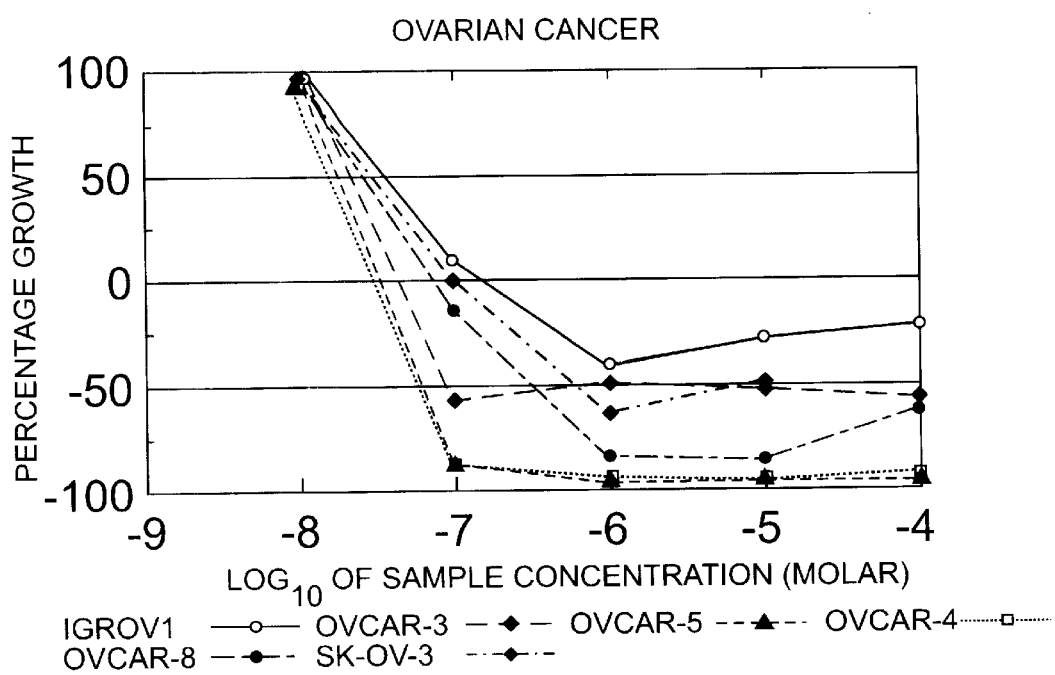
Figure 1I:
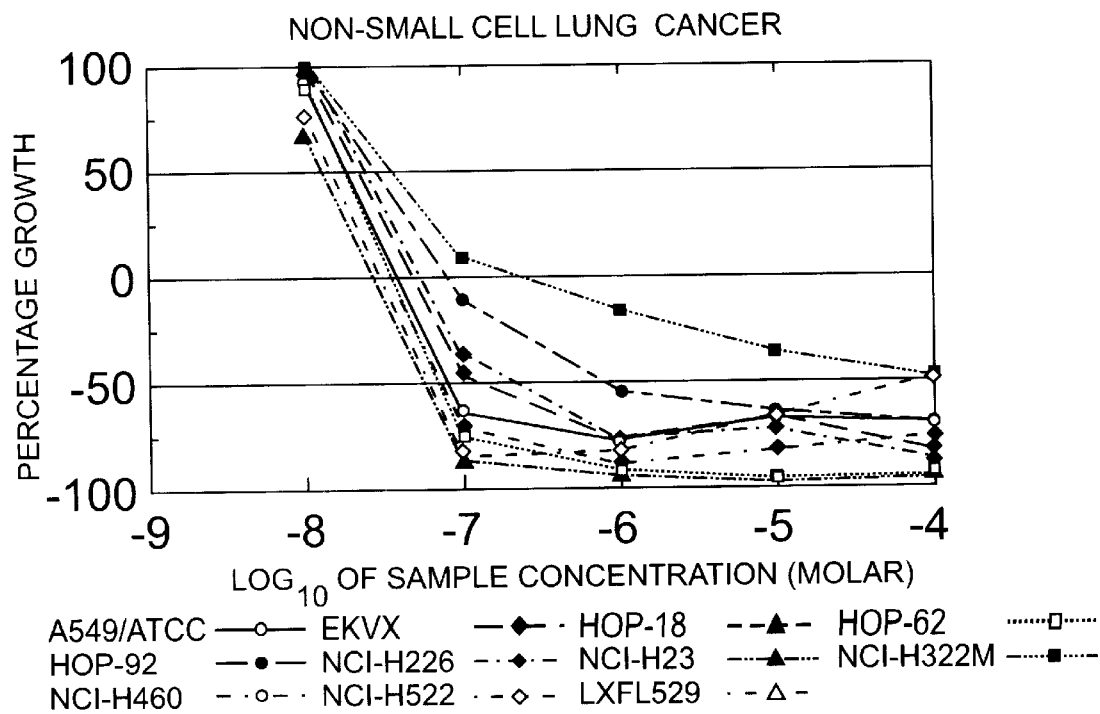
Figure 1J:
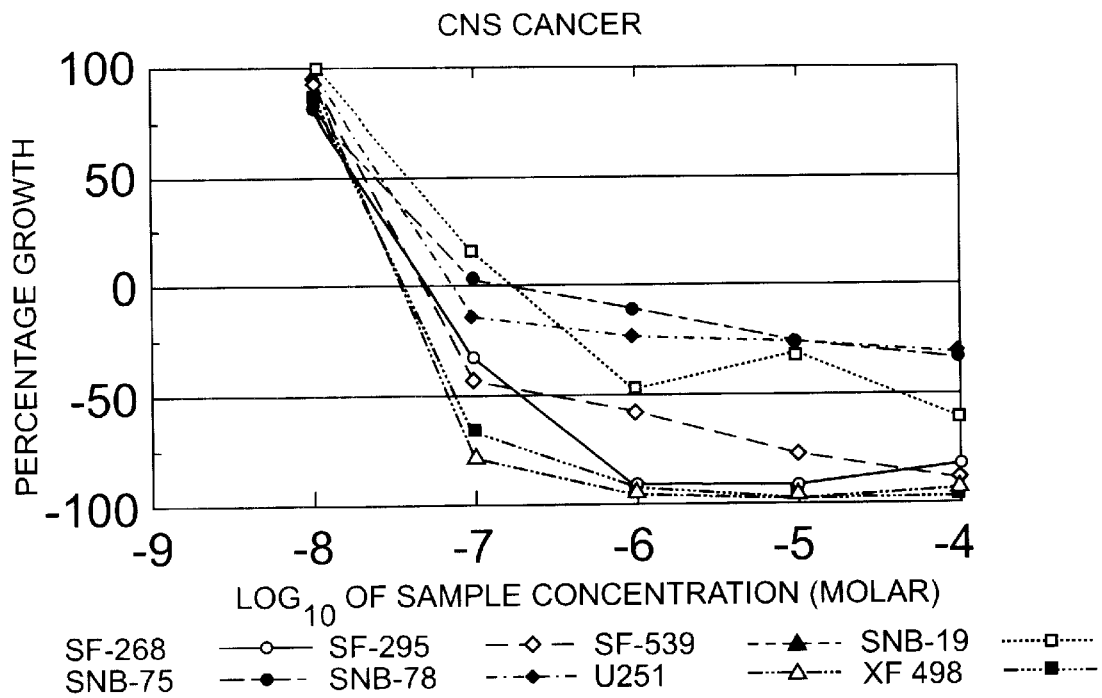
Figure 1K:
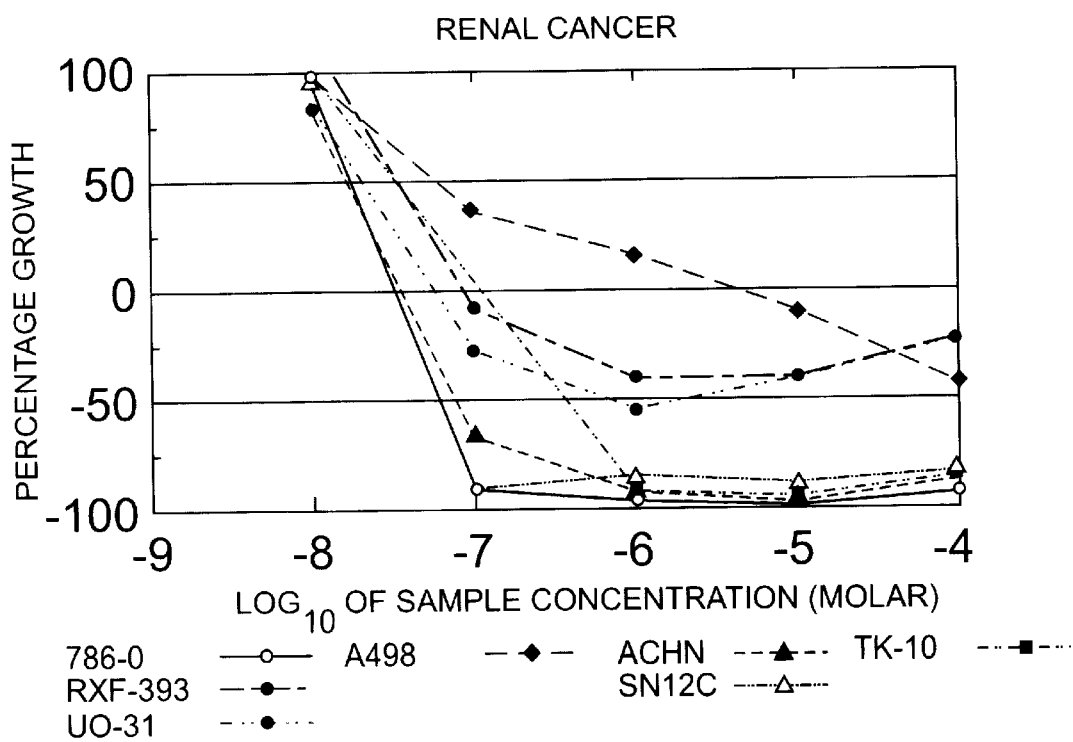
Figure 1L:
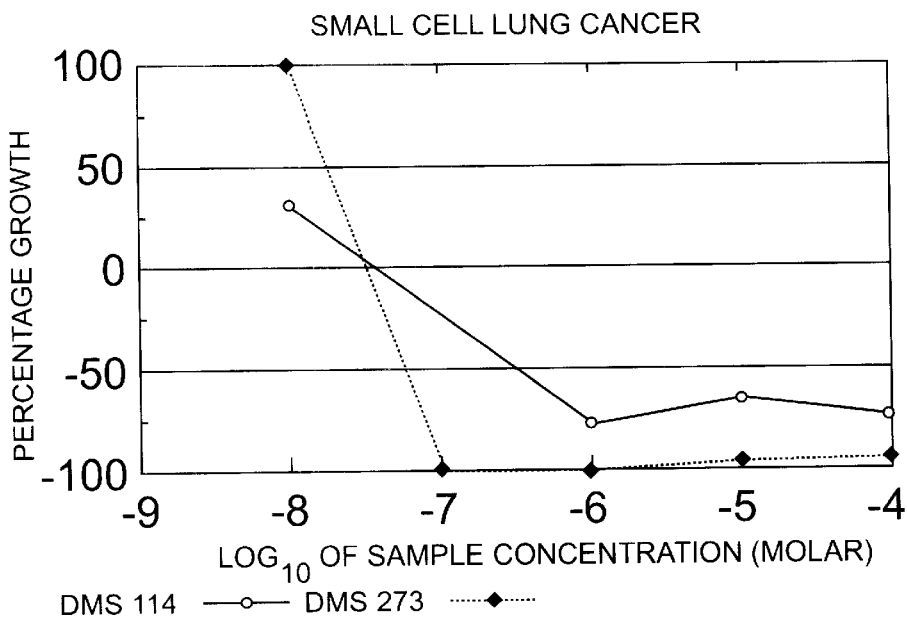
Figure 1M:
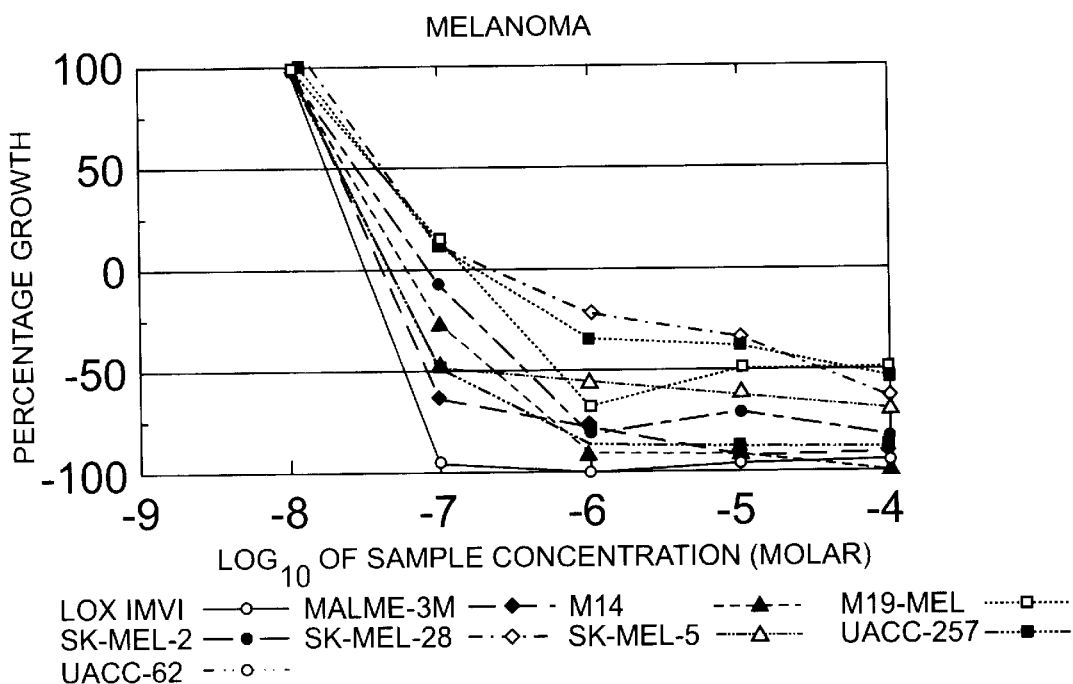
Figure 1N:
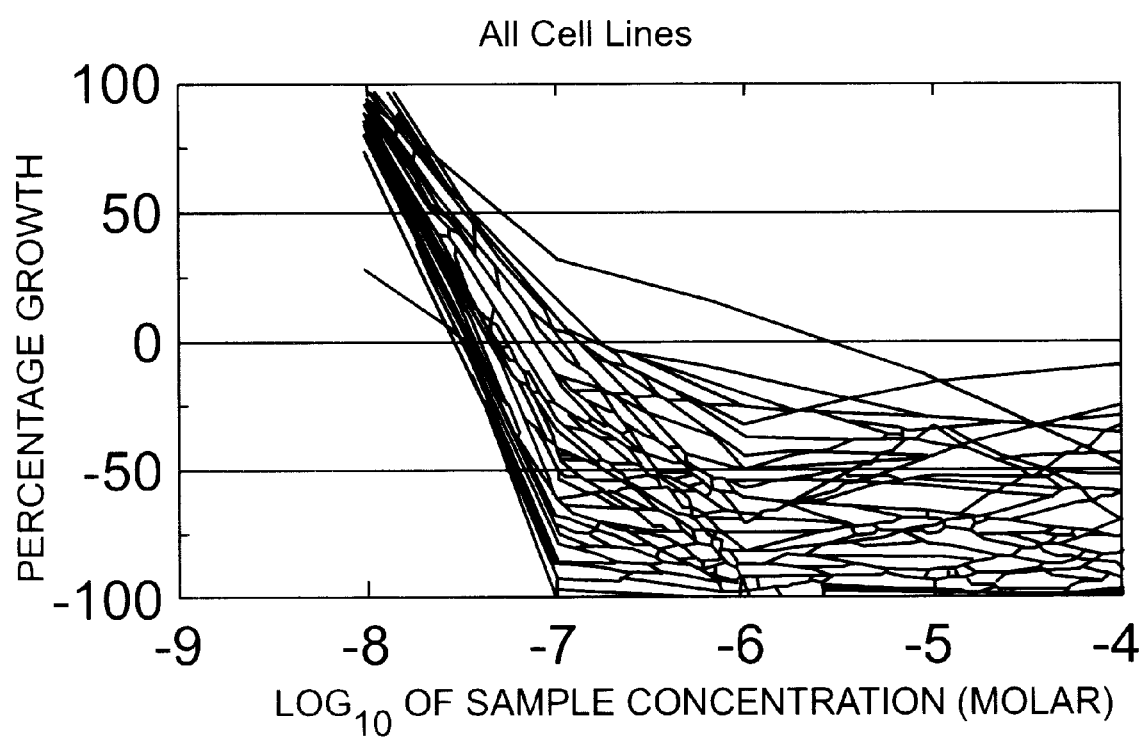
Figure 1O:
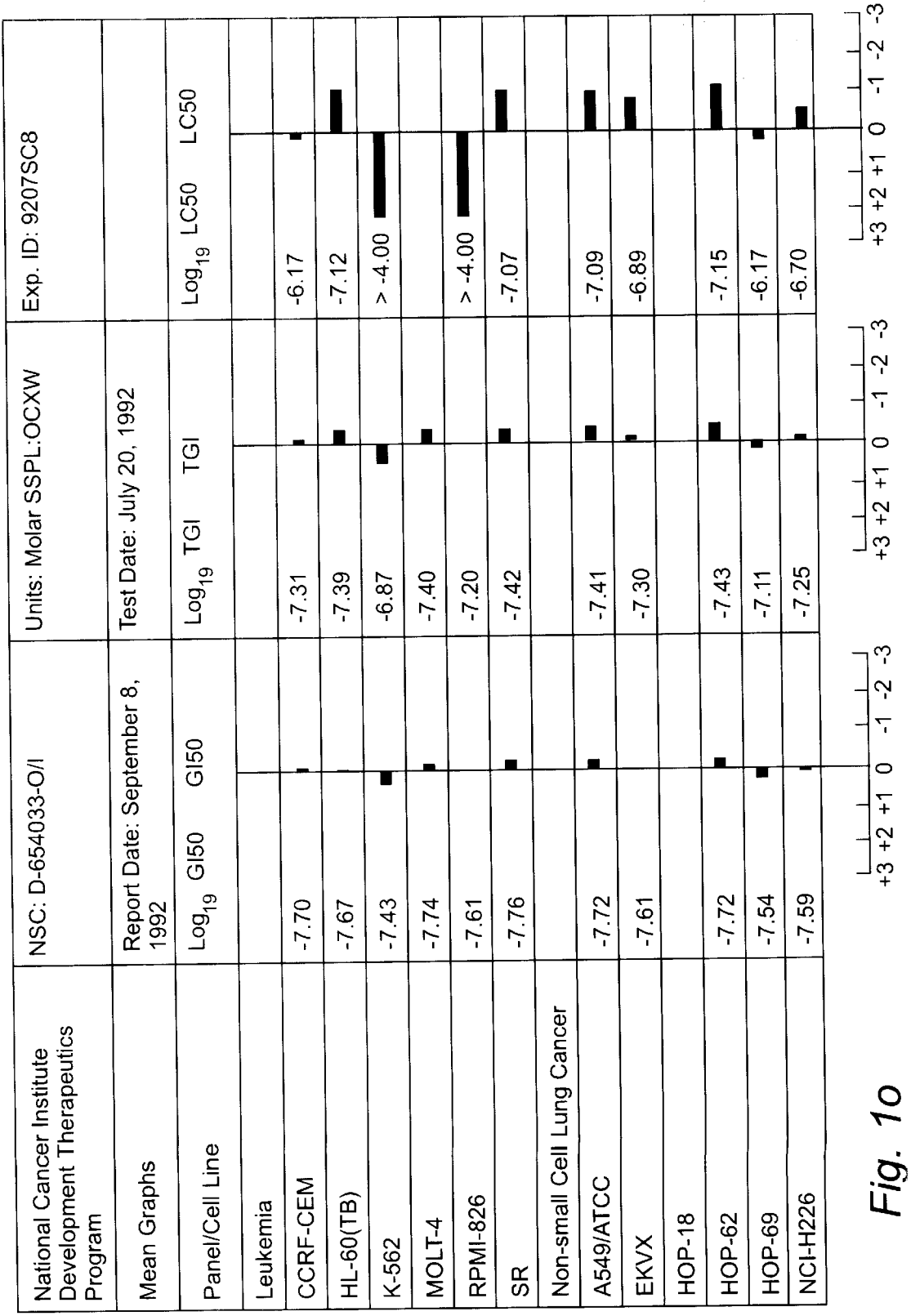
Figure 1P:
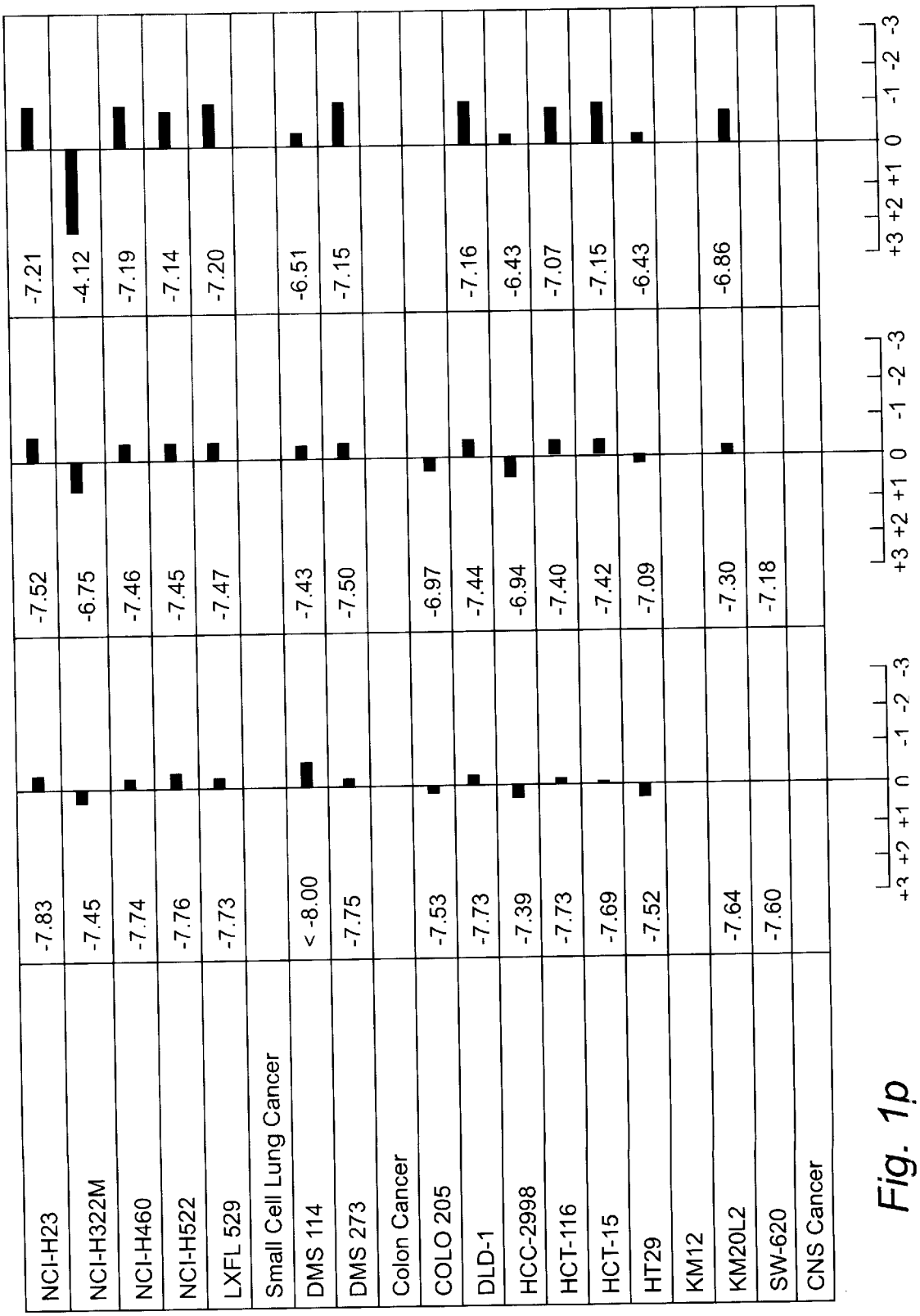
Figure 1Q:
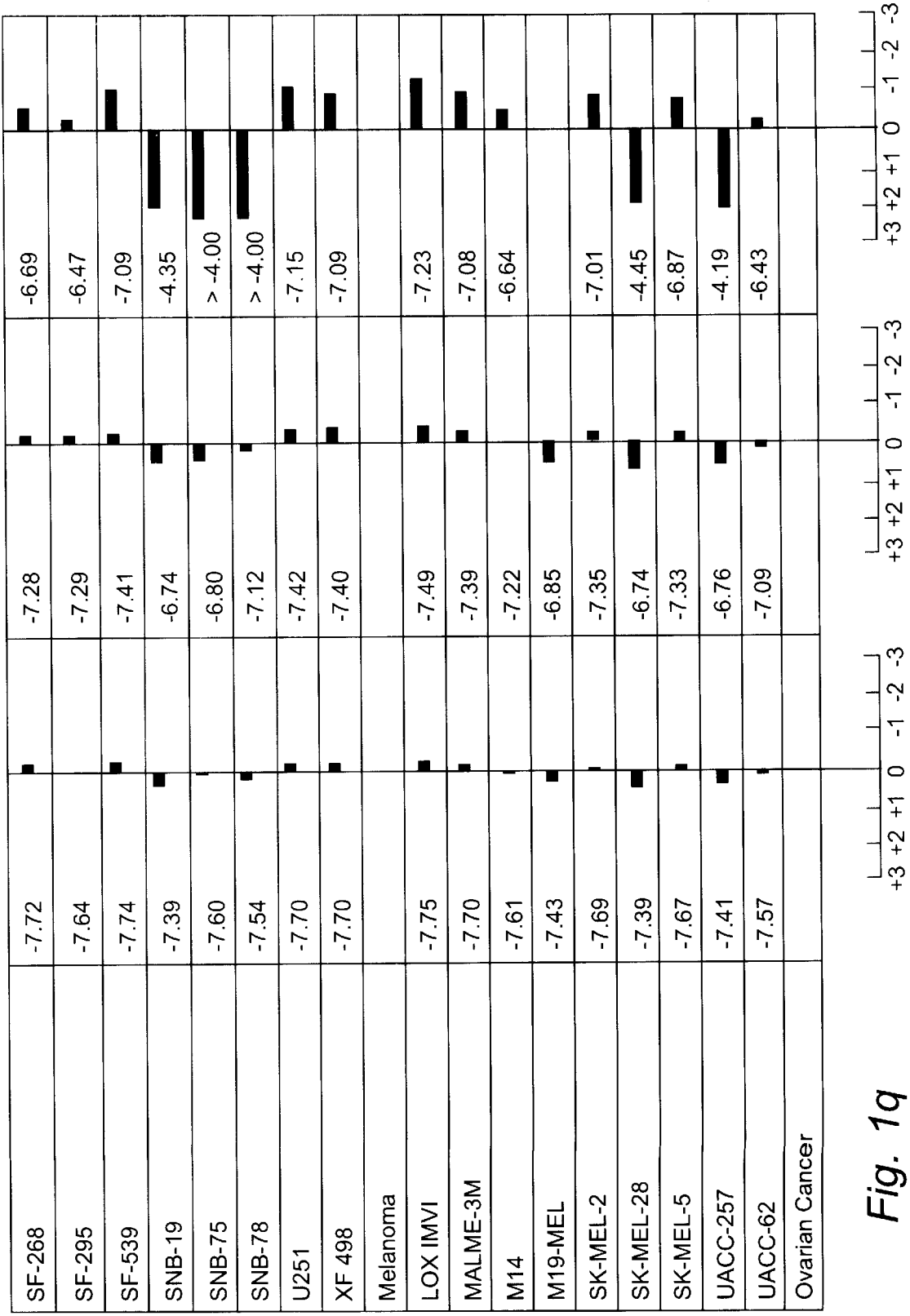
Figure 1R:
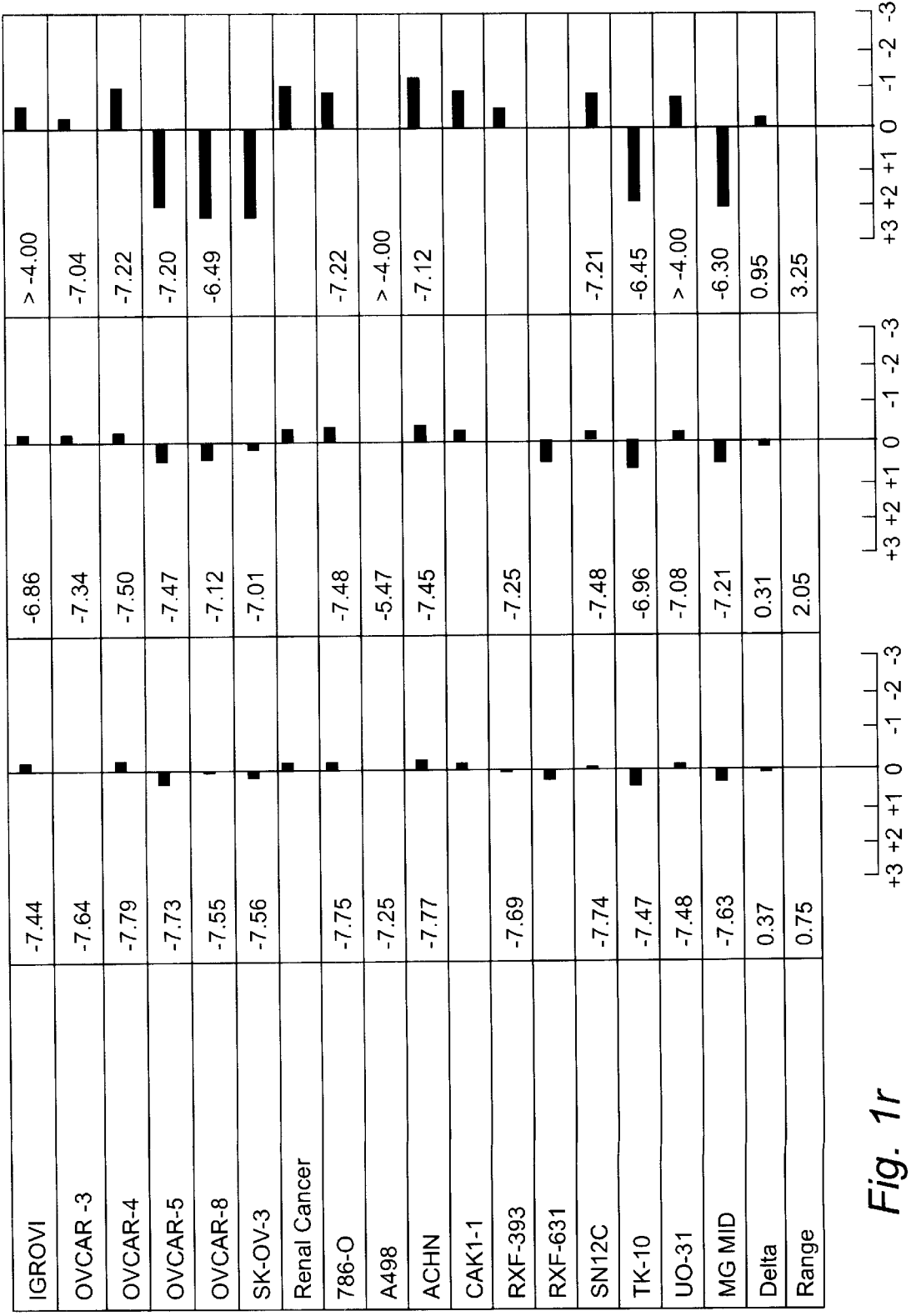
Figure 2A:
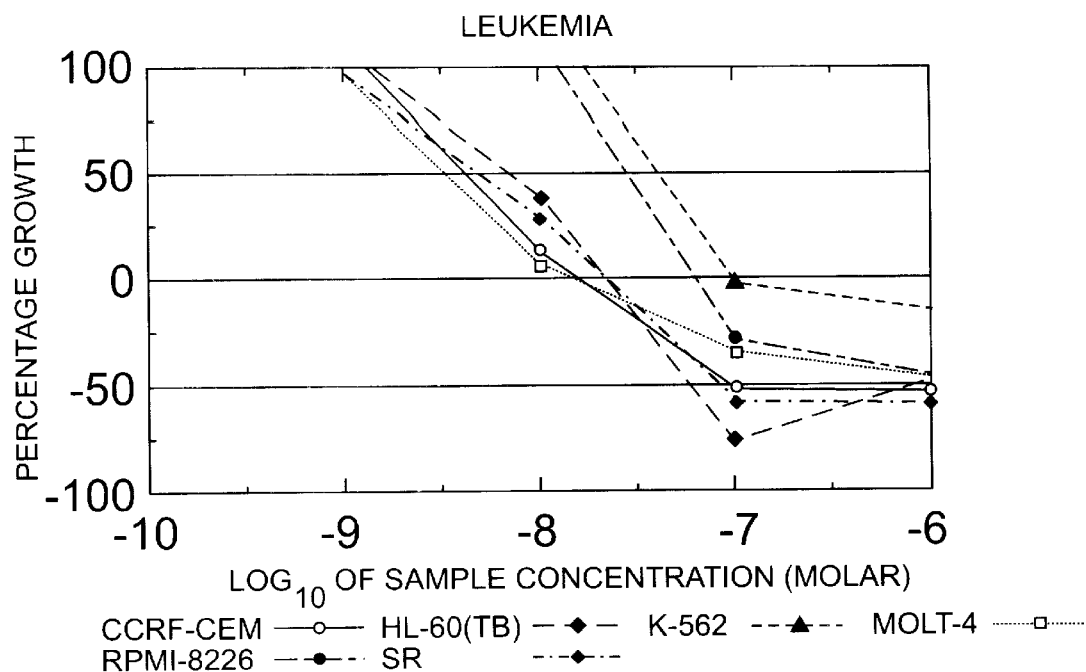
Figure 2B:
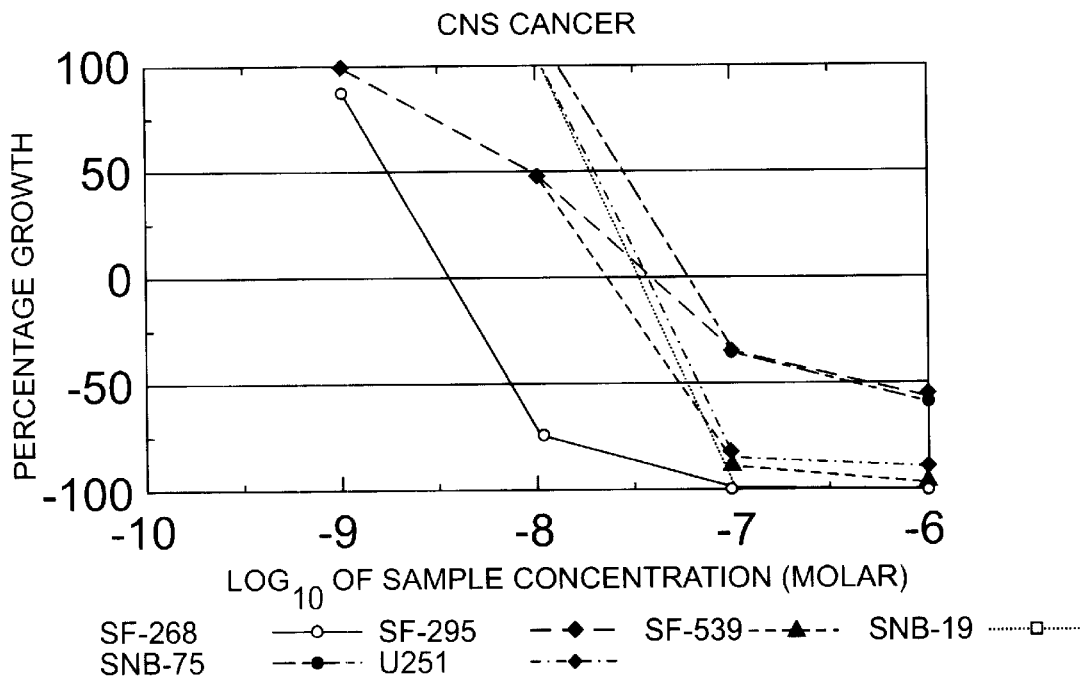
Figure 2C:
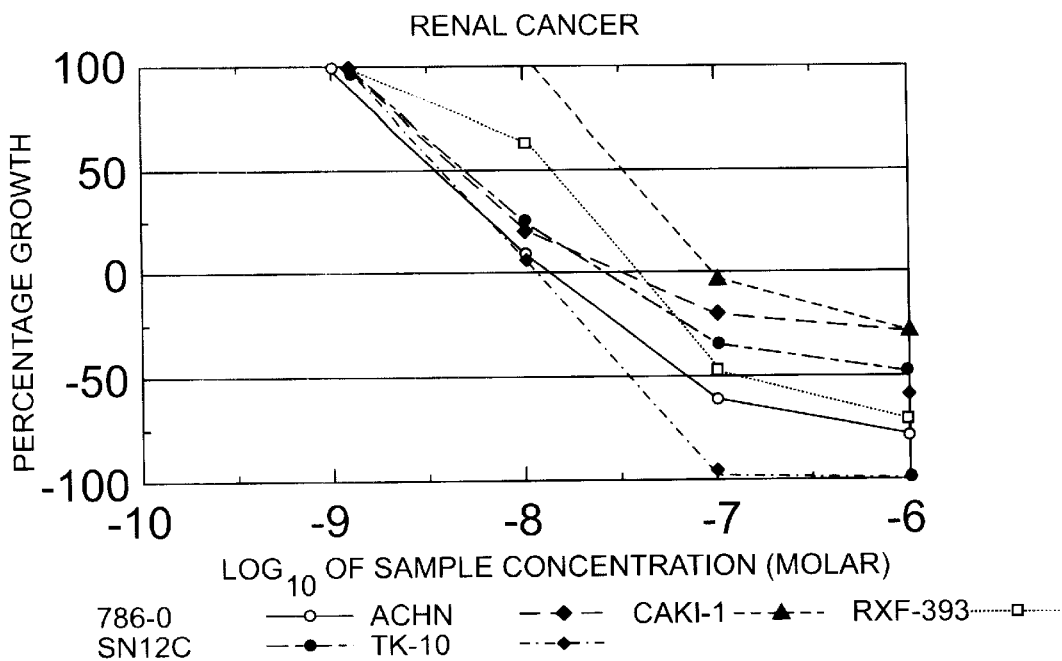
Figure 2D:
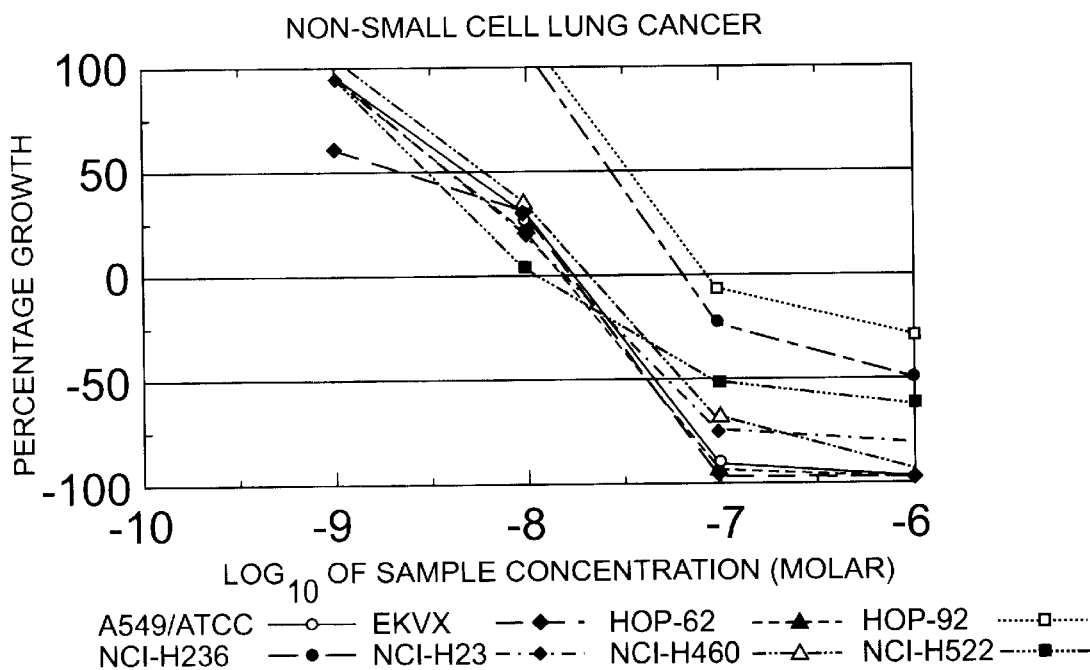
Figure 2E:
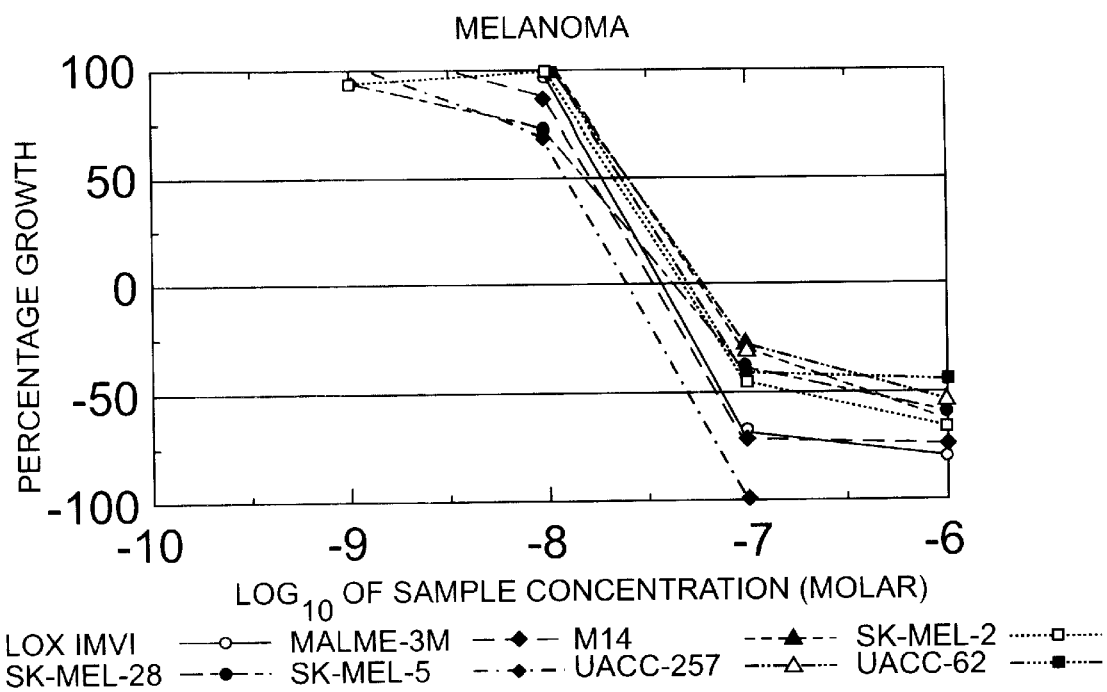
Figure 2F:
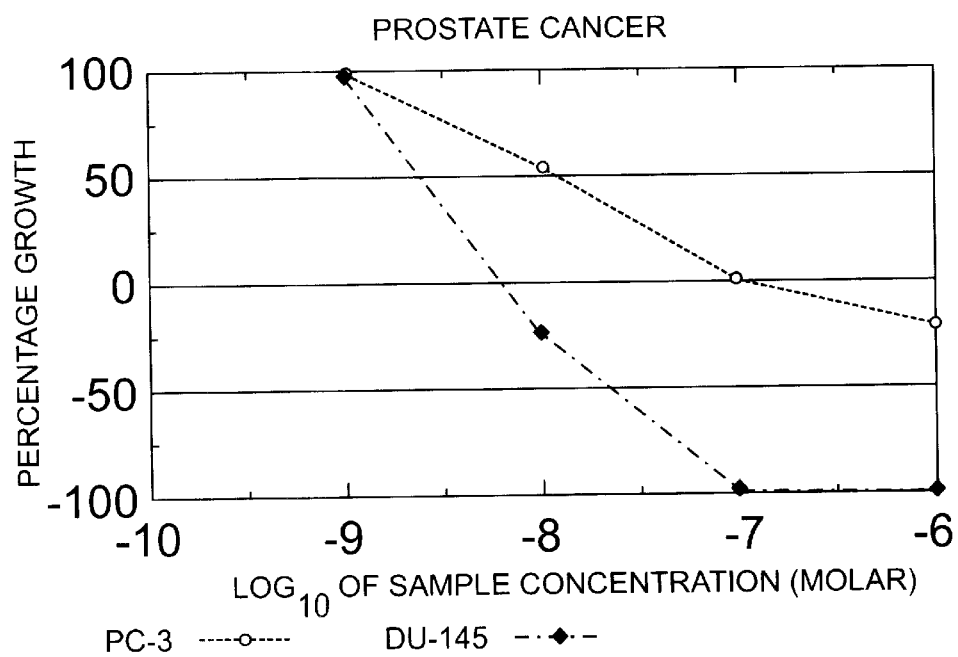
Figure 2G:
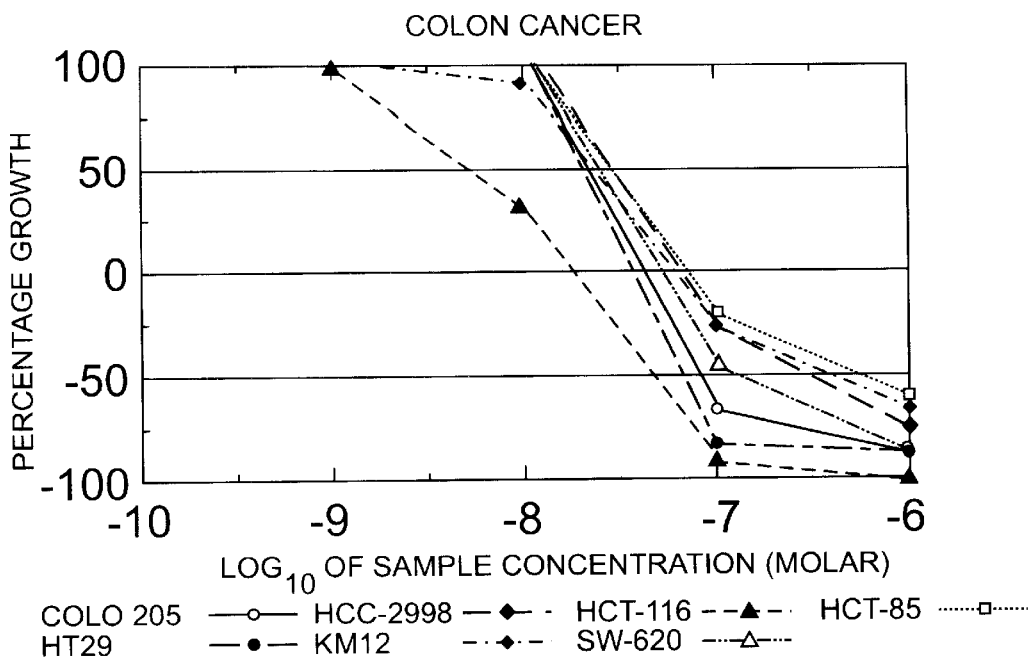
Figure 2H:
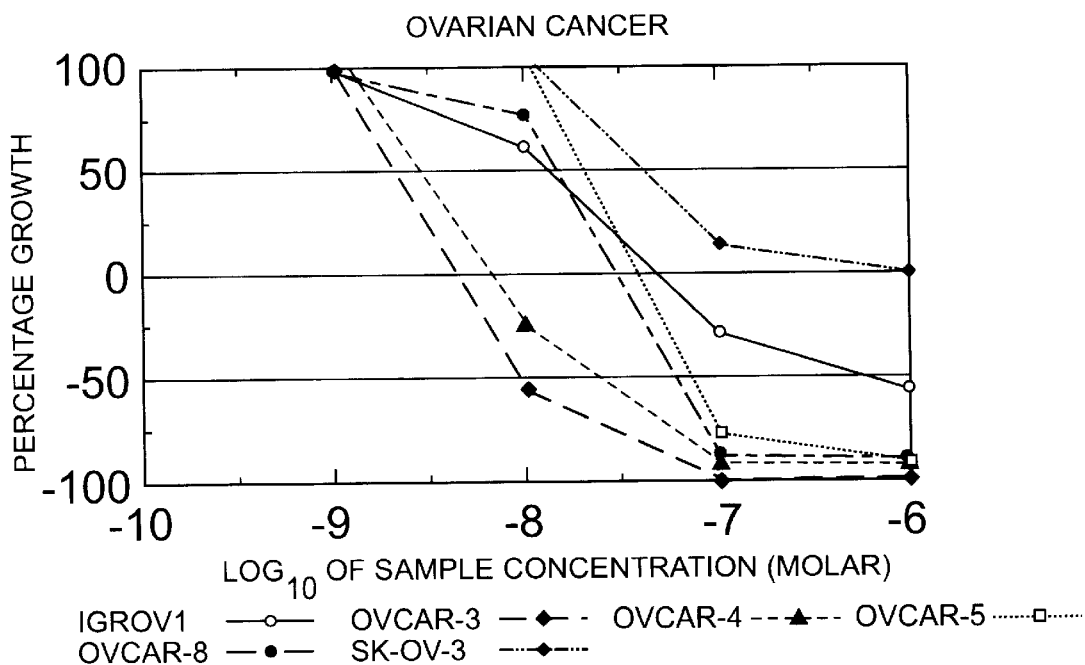
Figure 2I:
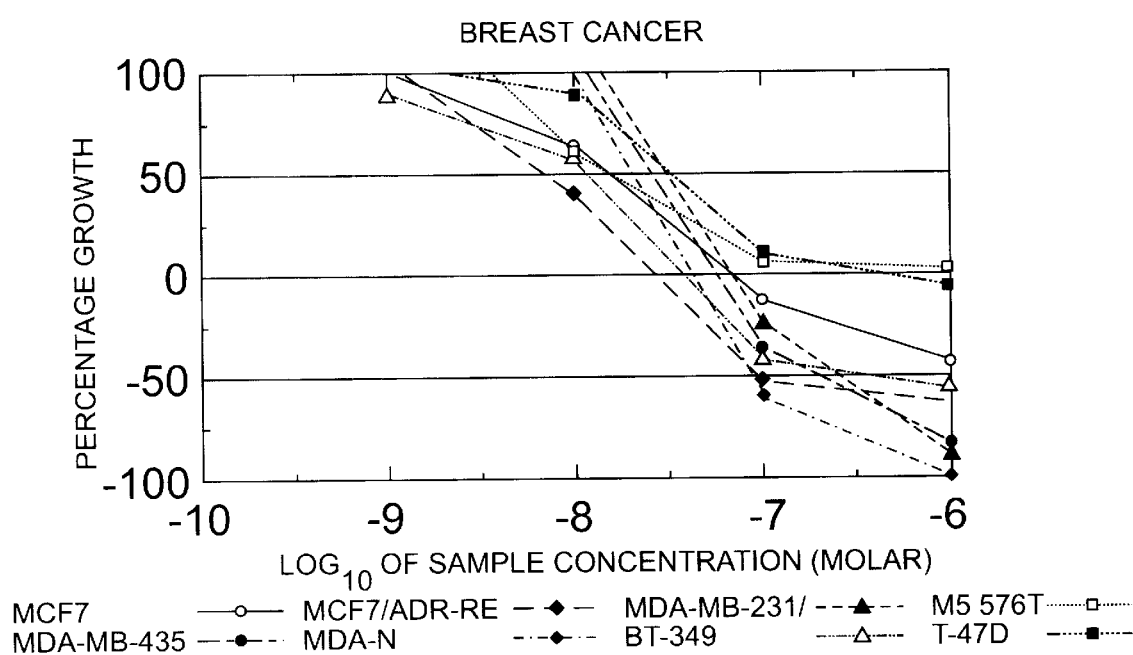
Figure 2J:
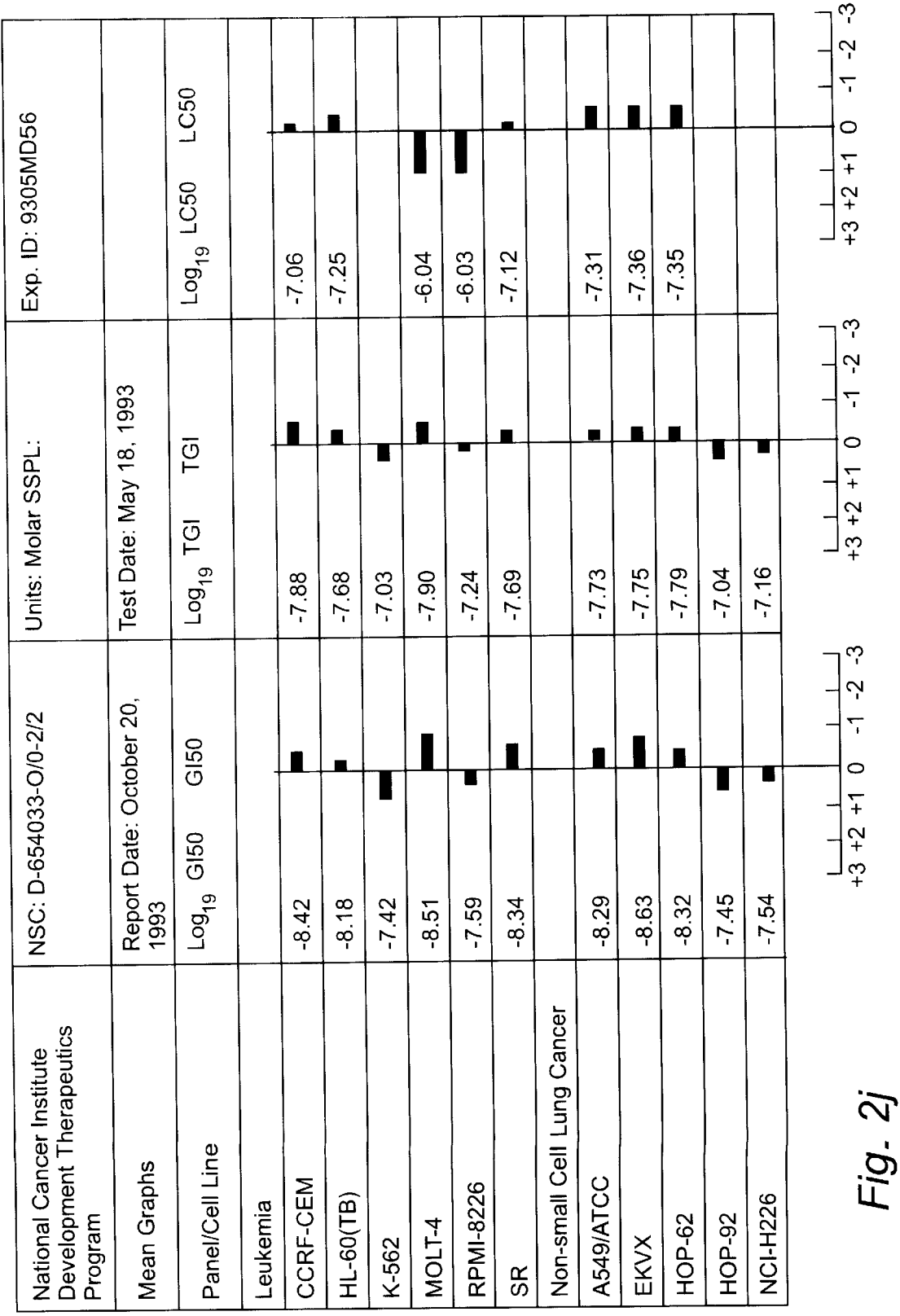
Figure 2K:
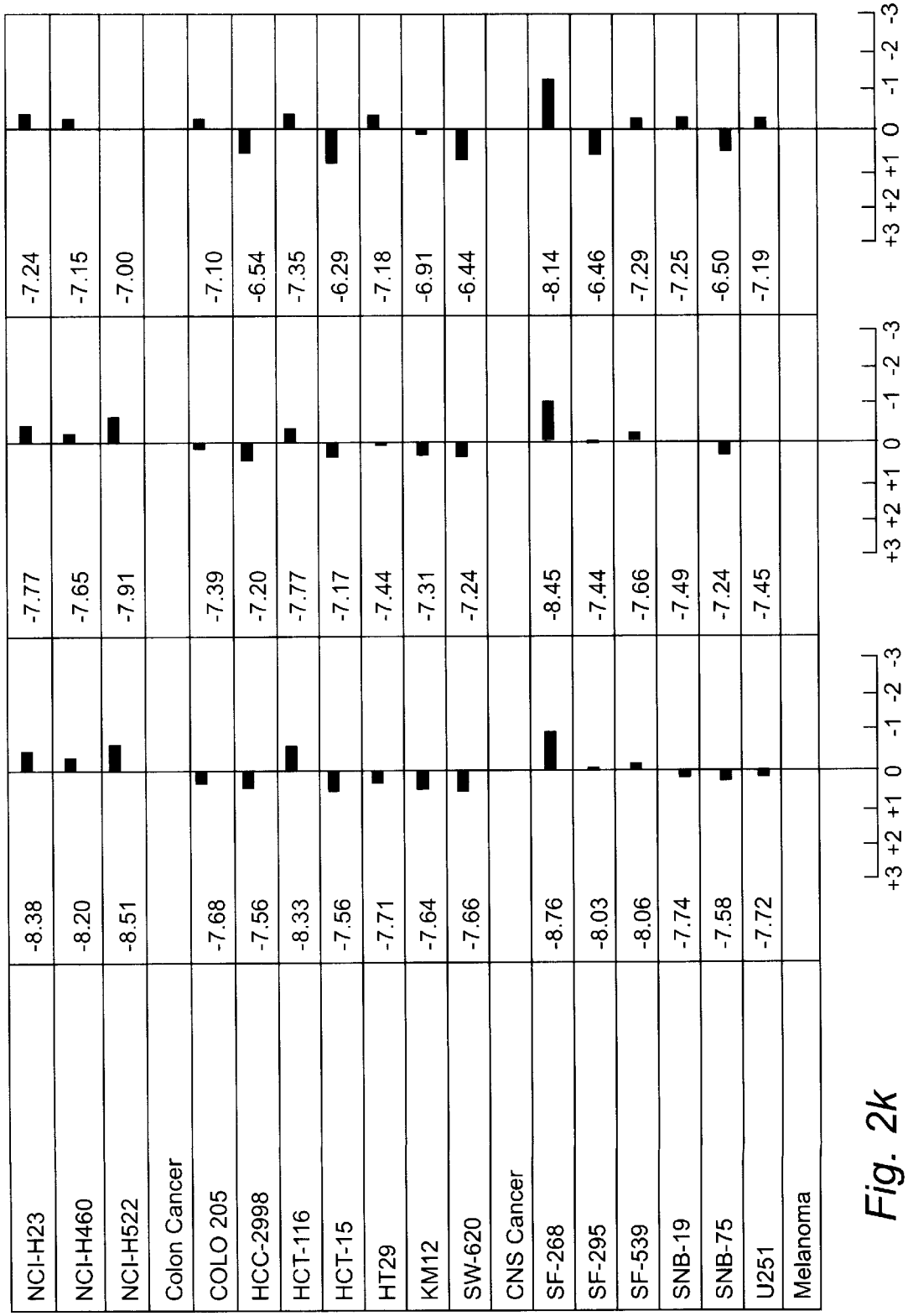
Figure 21:
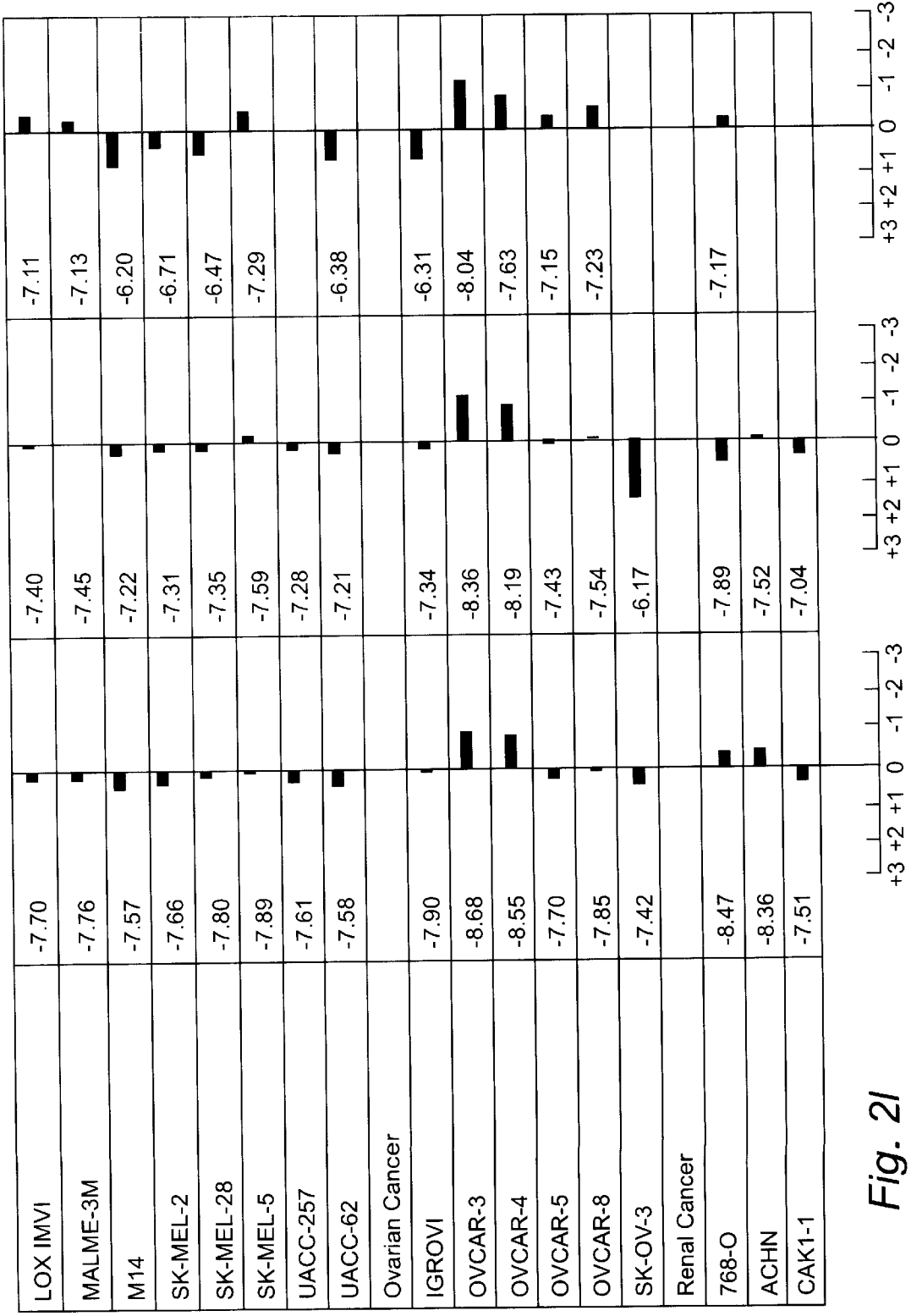
Figure 2M:
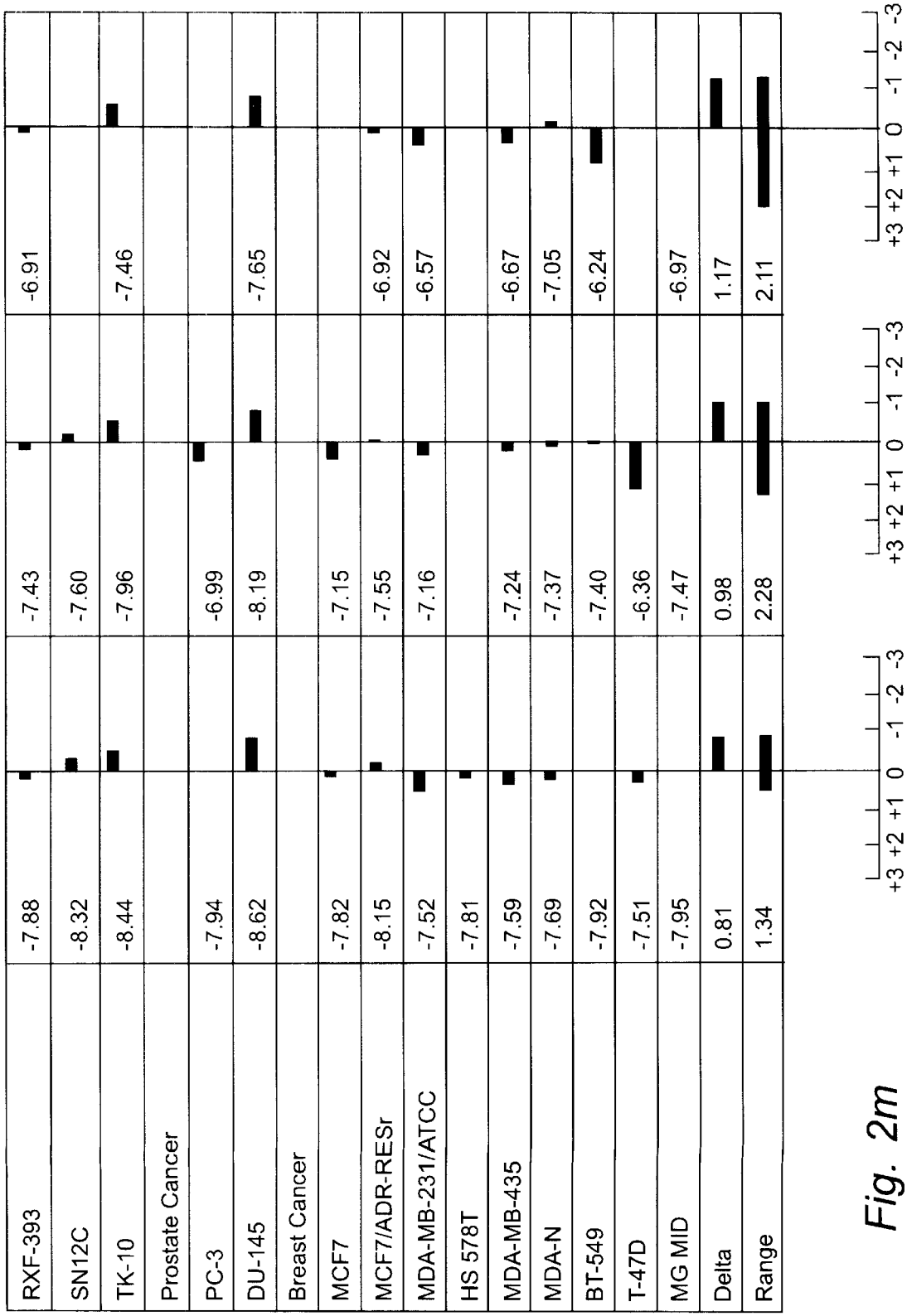
Figure 3A:
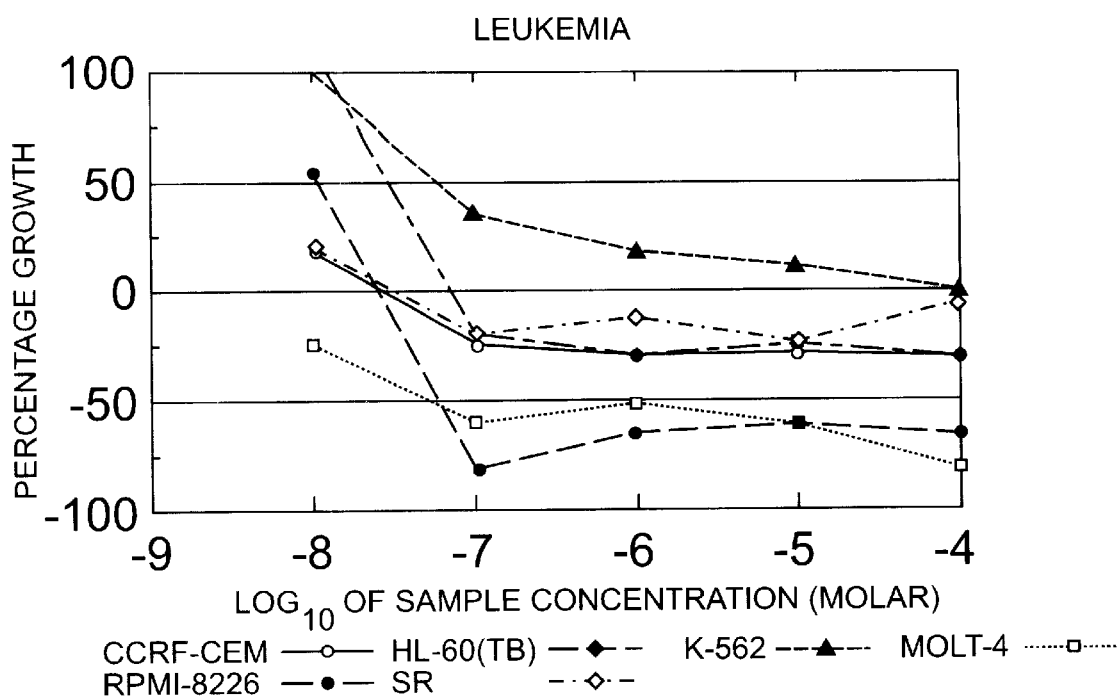
Figure 3B:
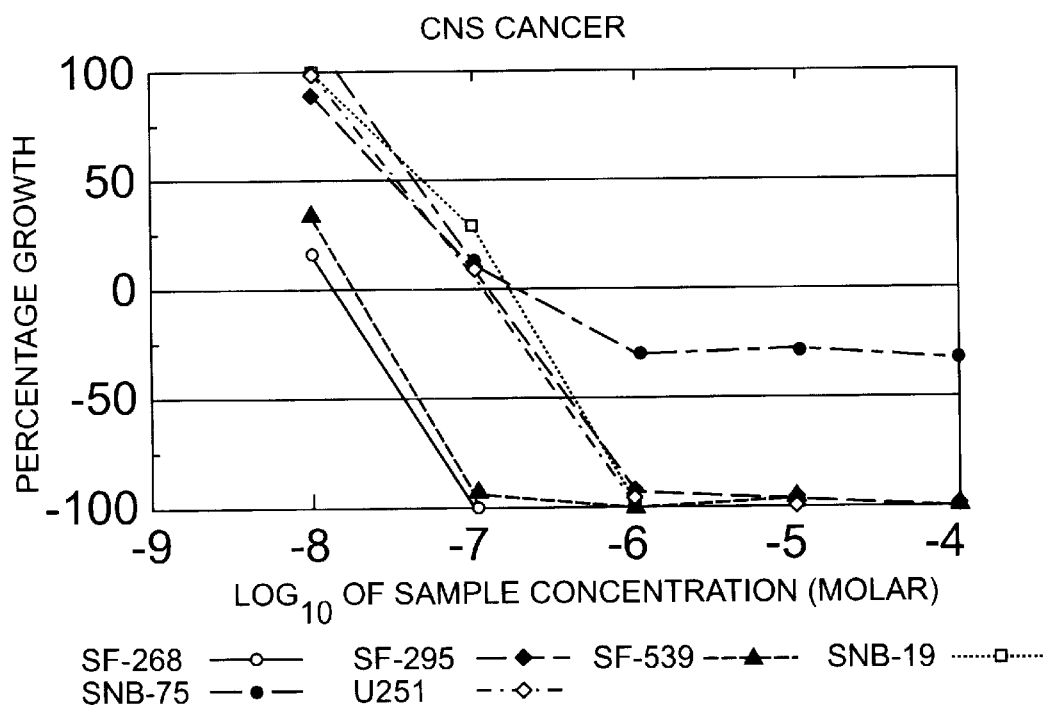
Figure 3C:
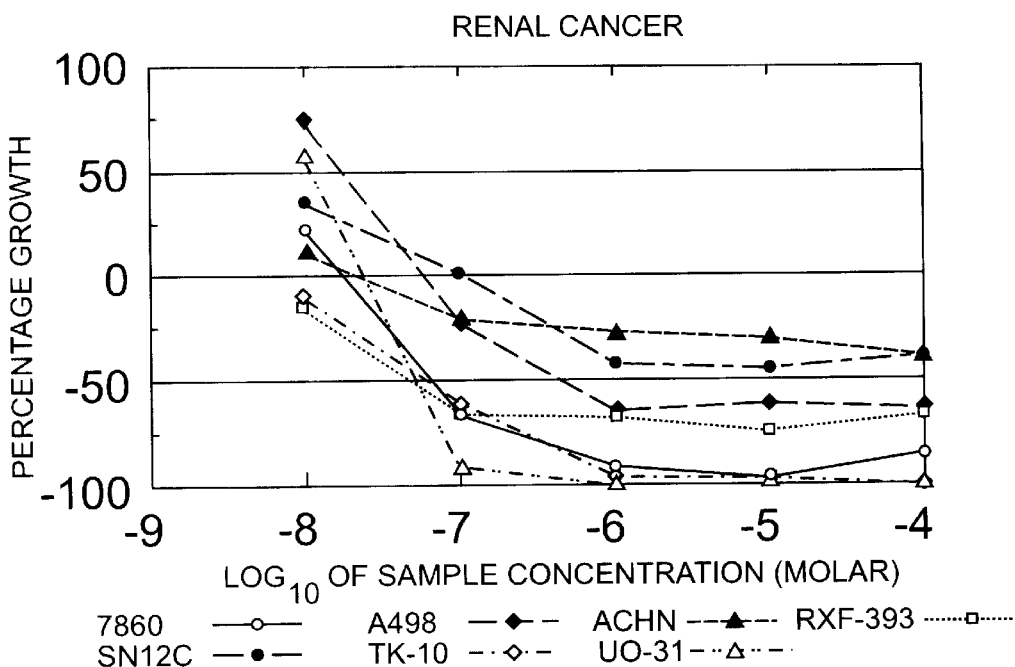
Figure 3D:
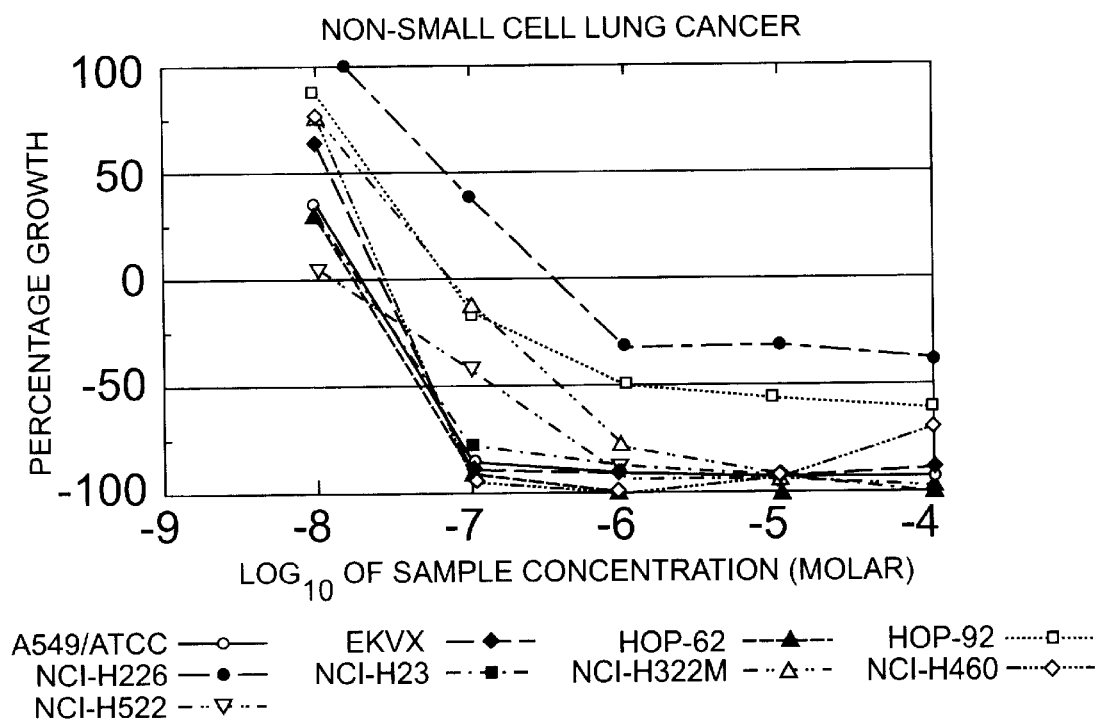
Figure 3E:
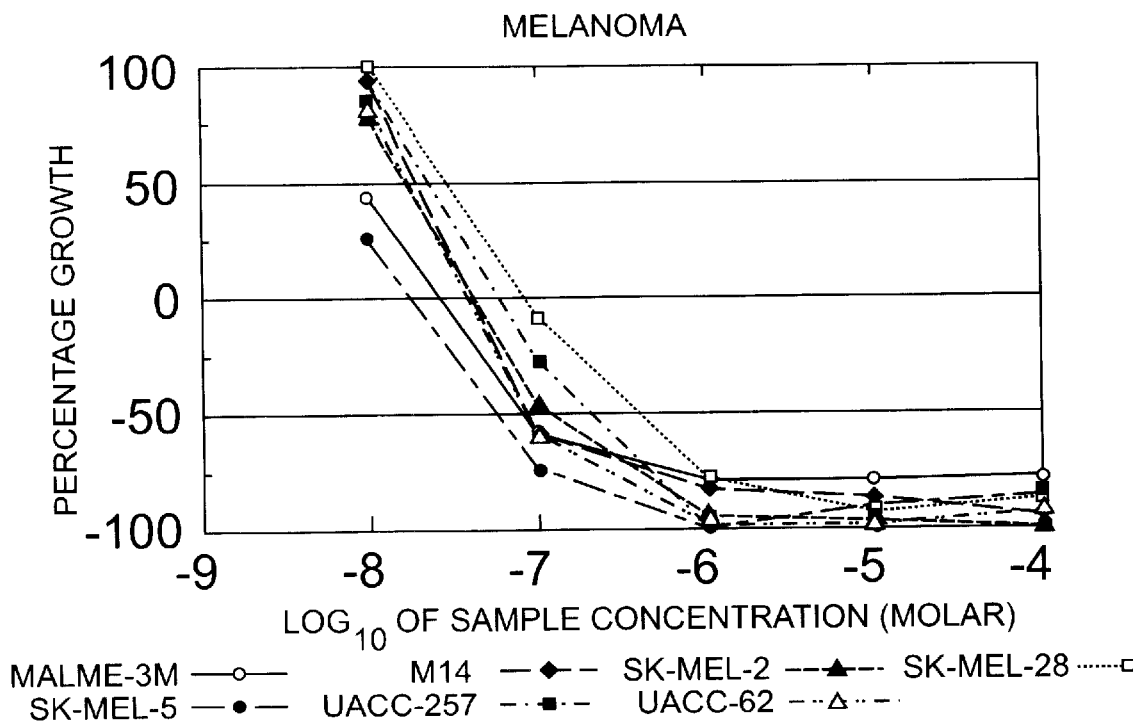
Figure 3F:
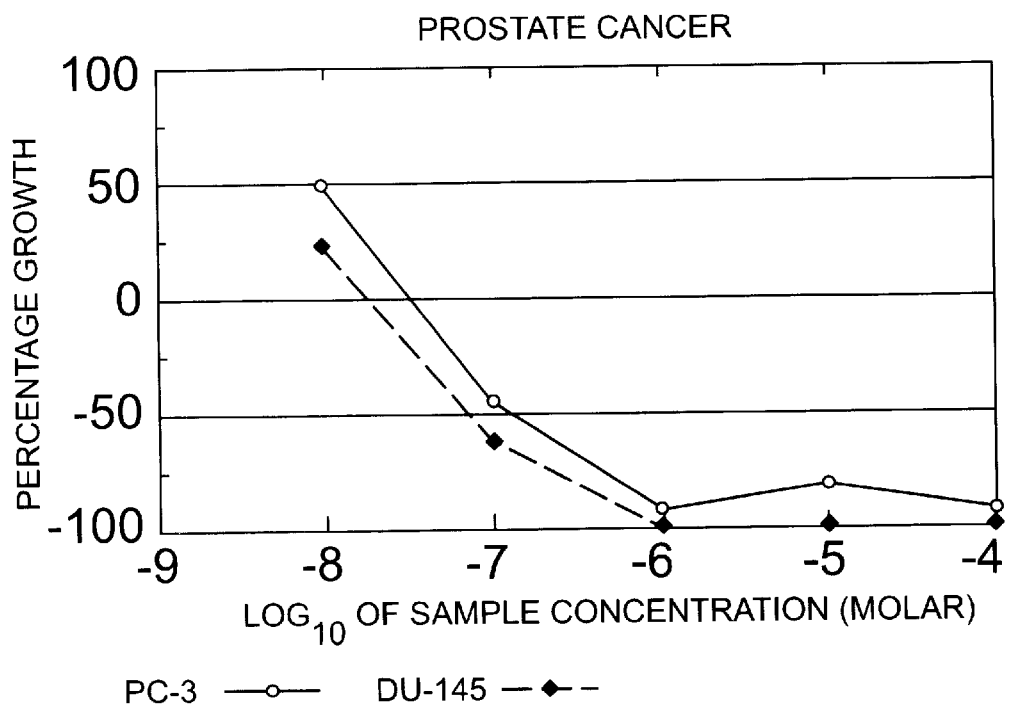
Figure 3G:
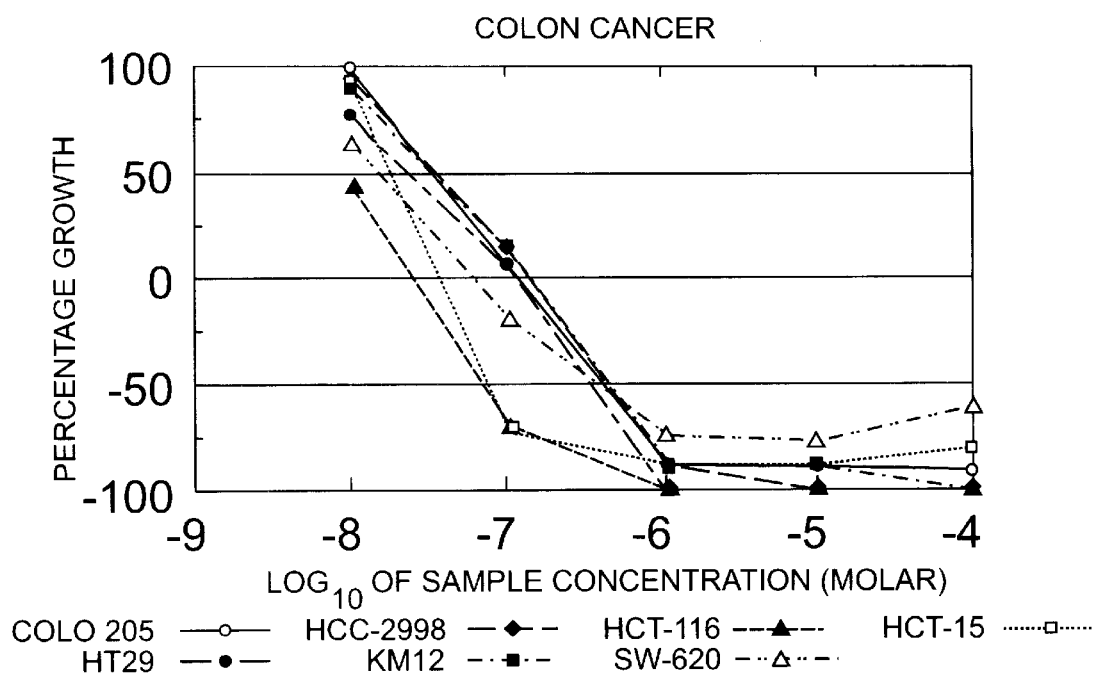
Figure 3H:
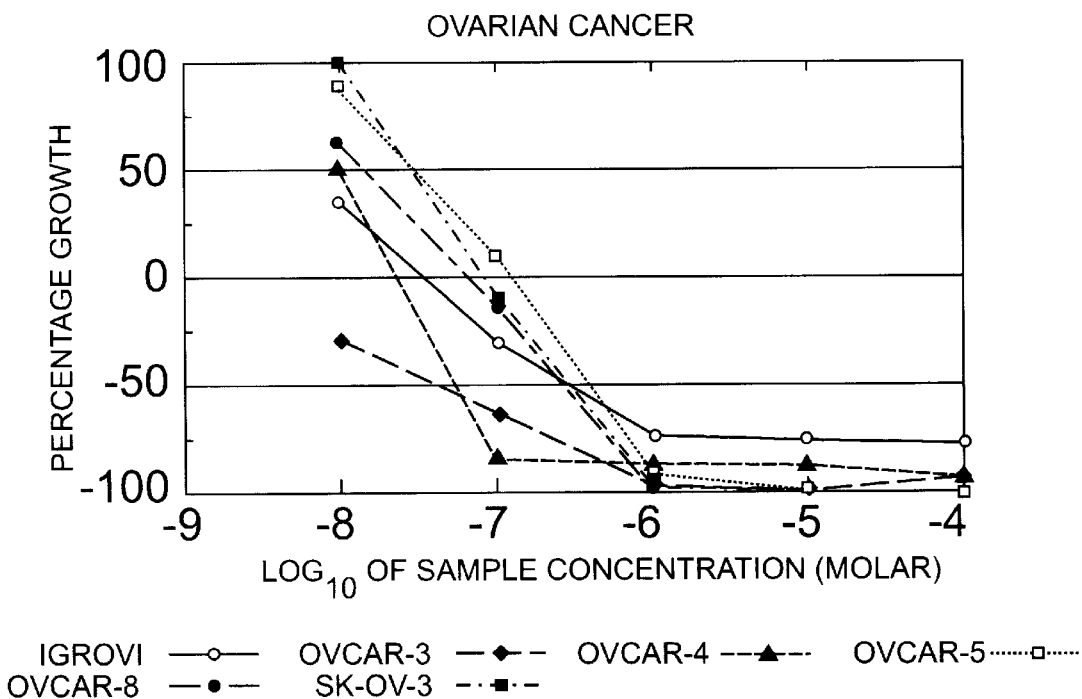
Figure 3I:
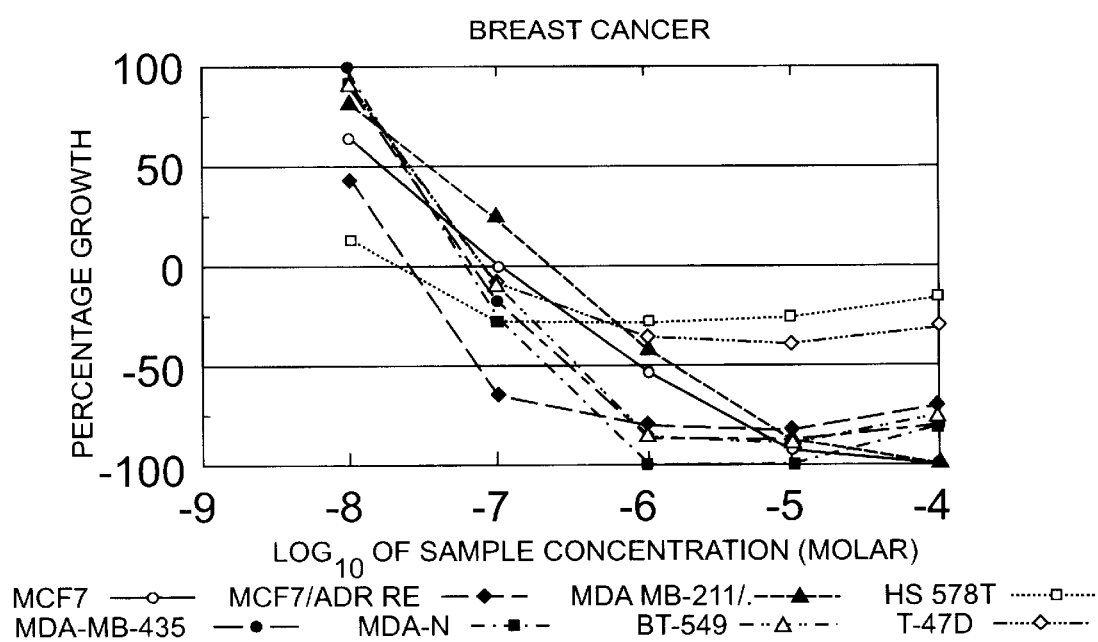
Figure 3J:
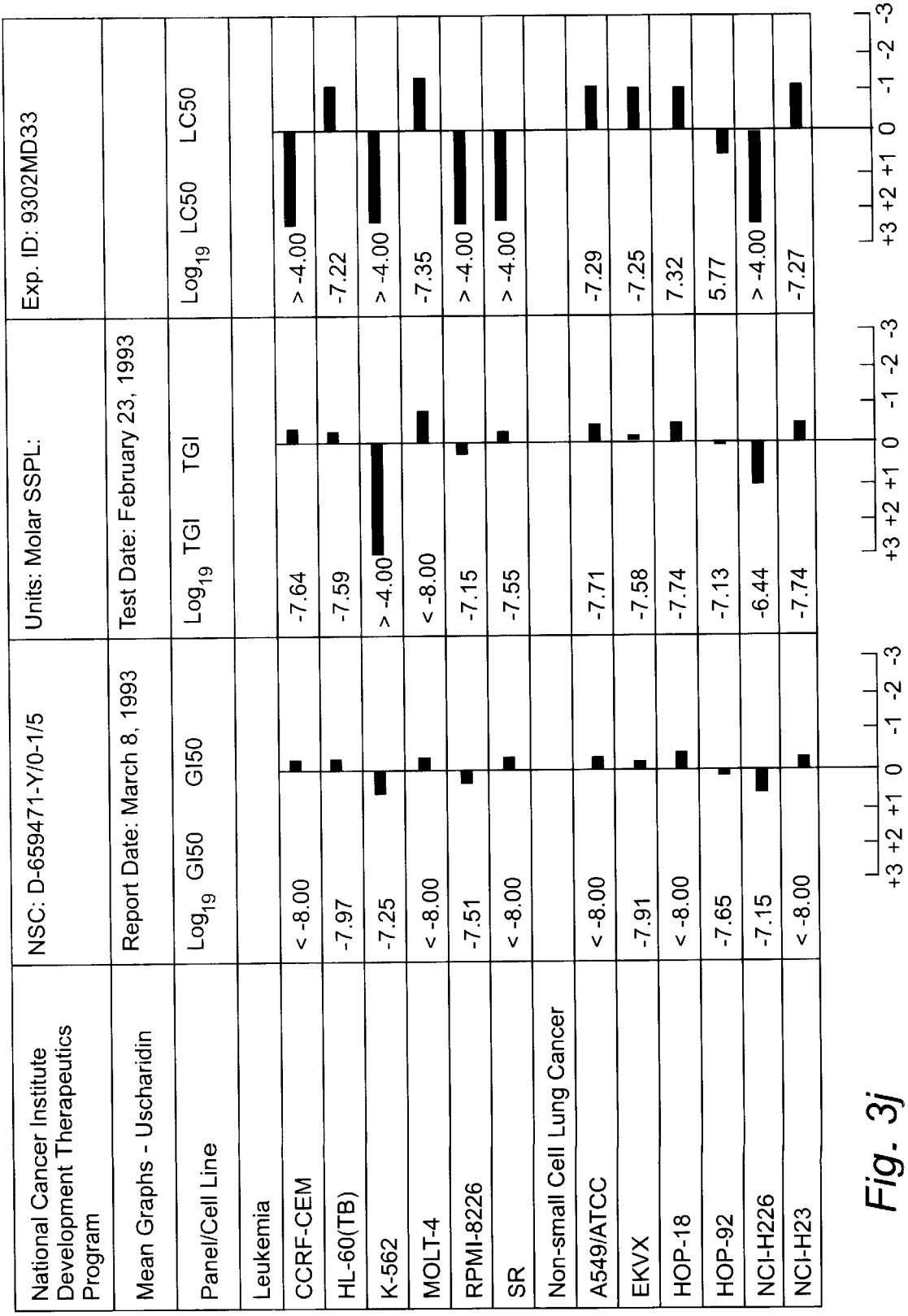
Figure 3K:
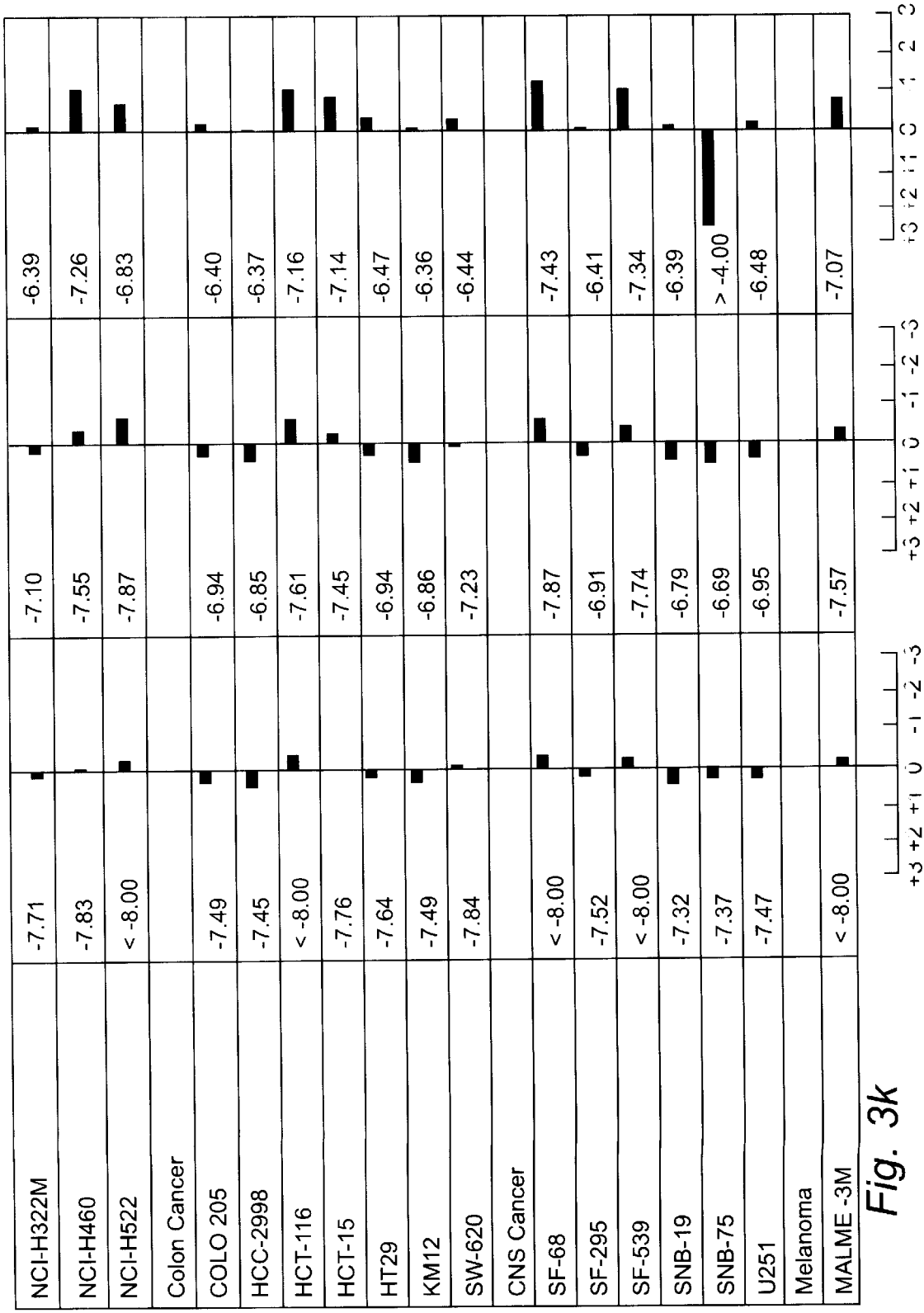
Figure 31:
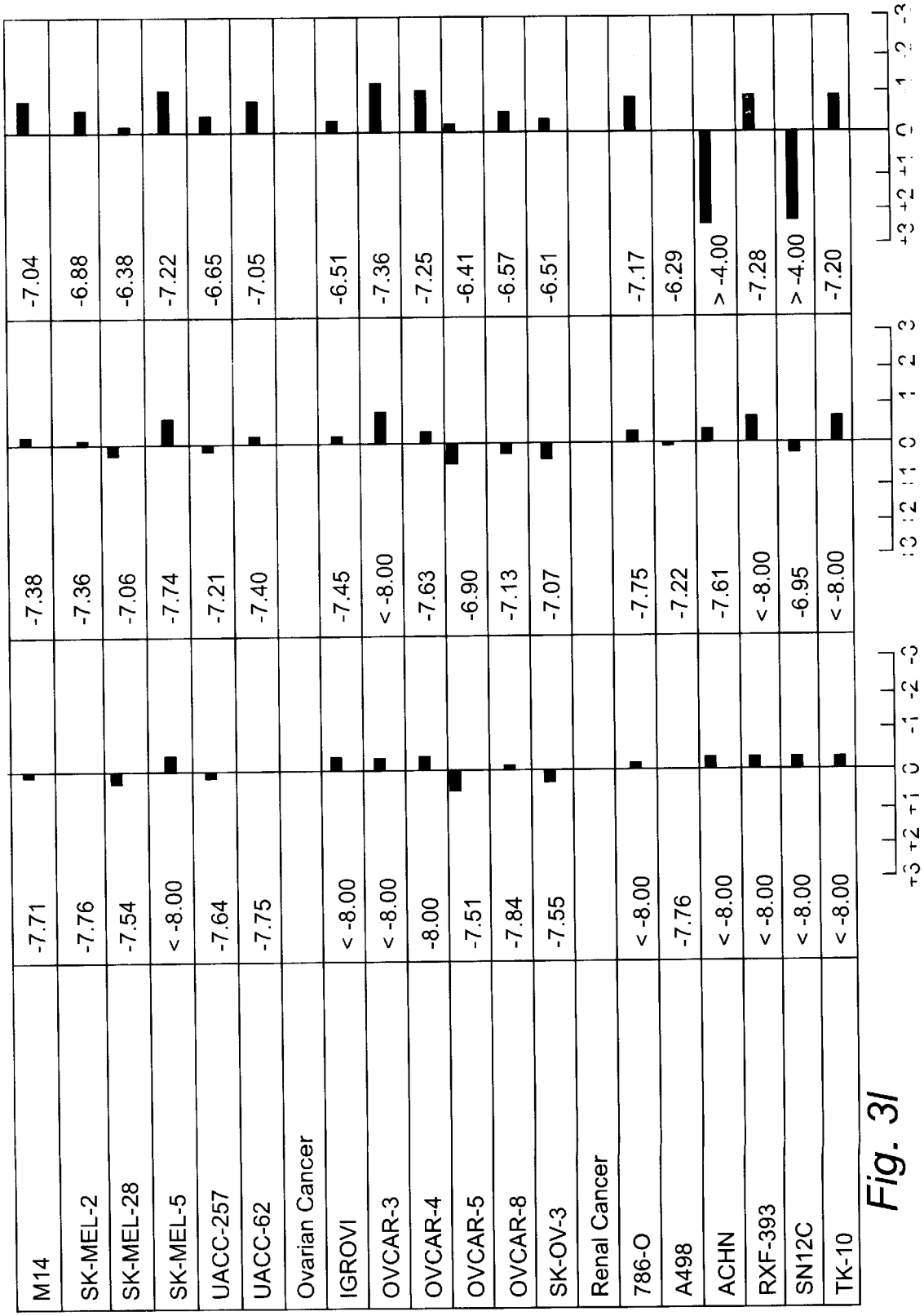
Figure 3M:
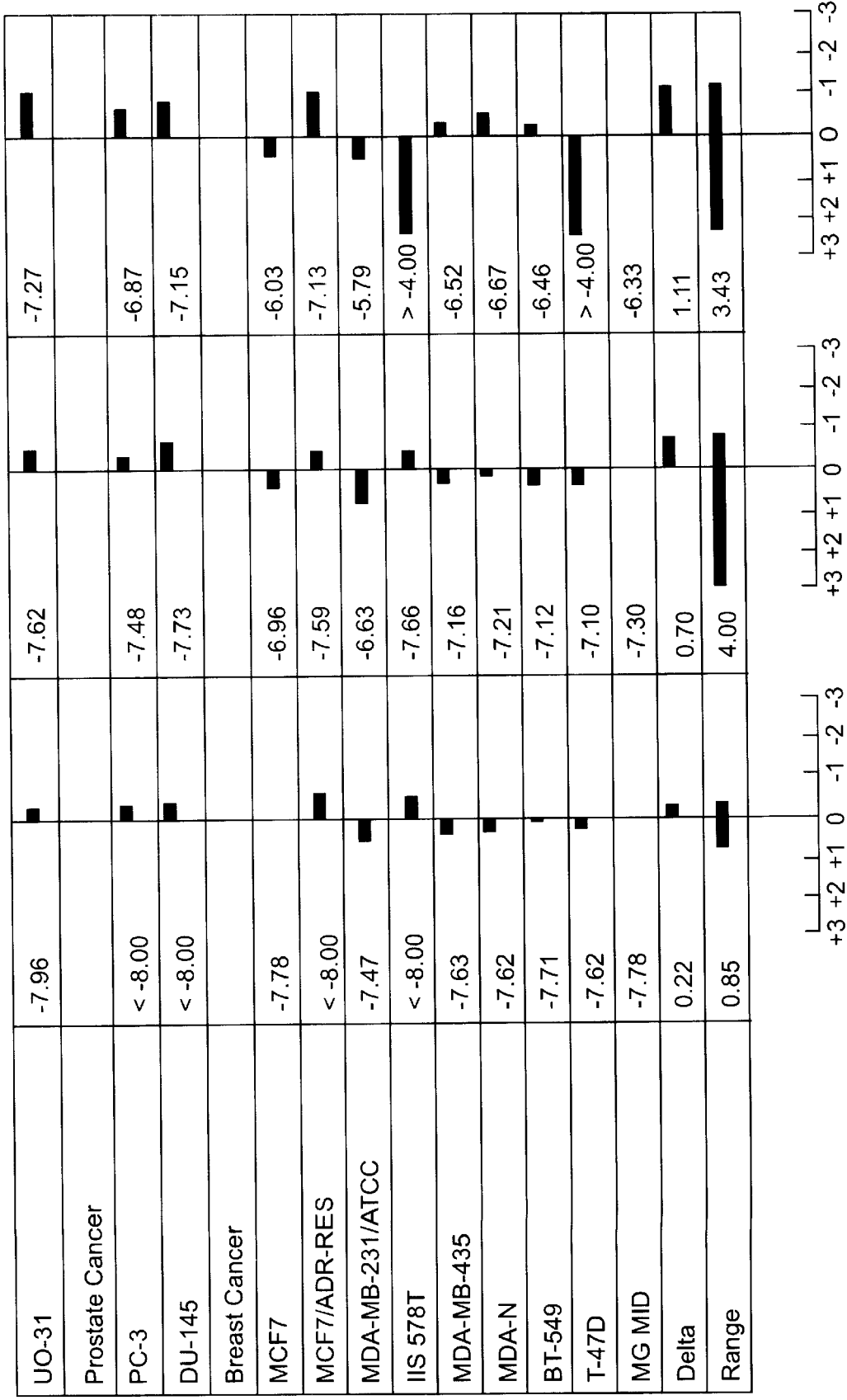
Figure 4A:
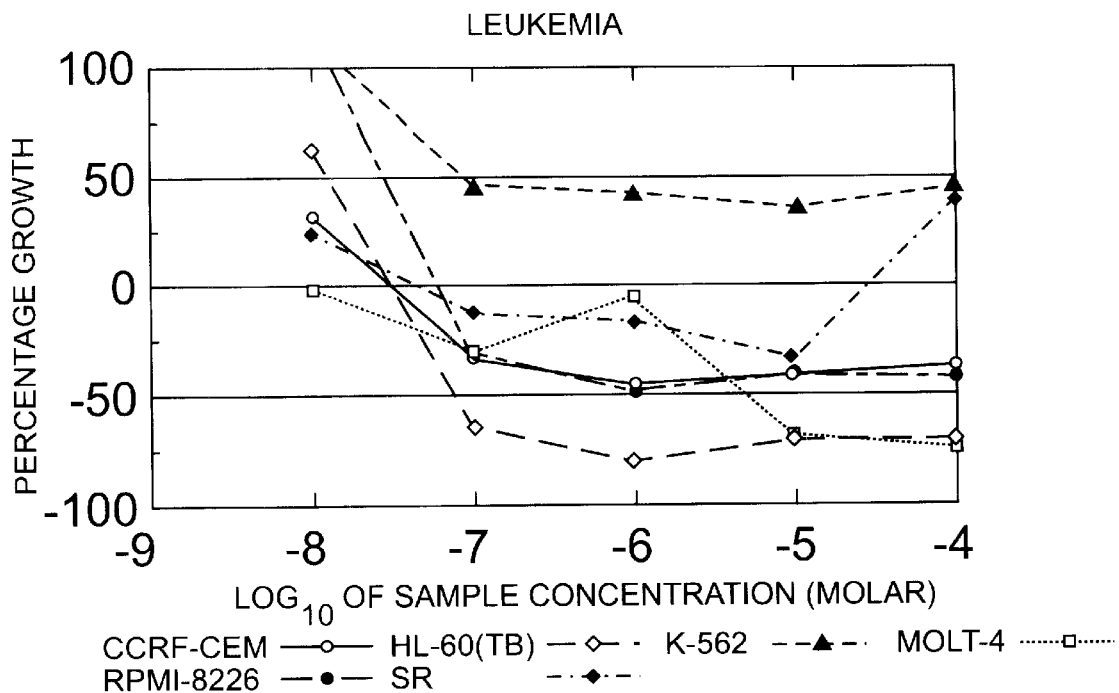
Figure 4B:
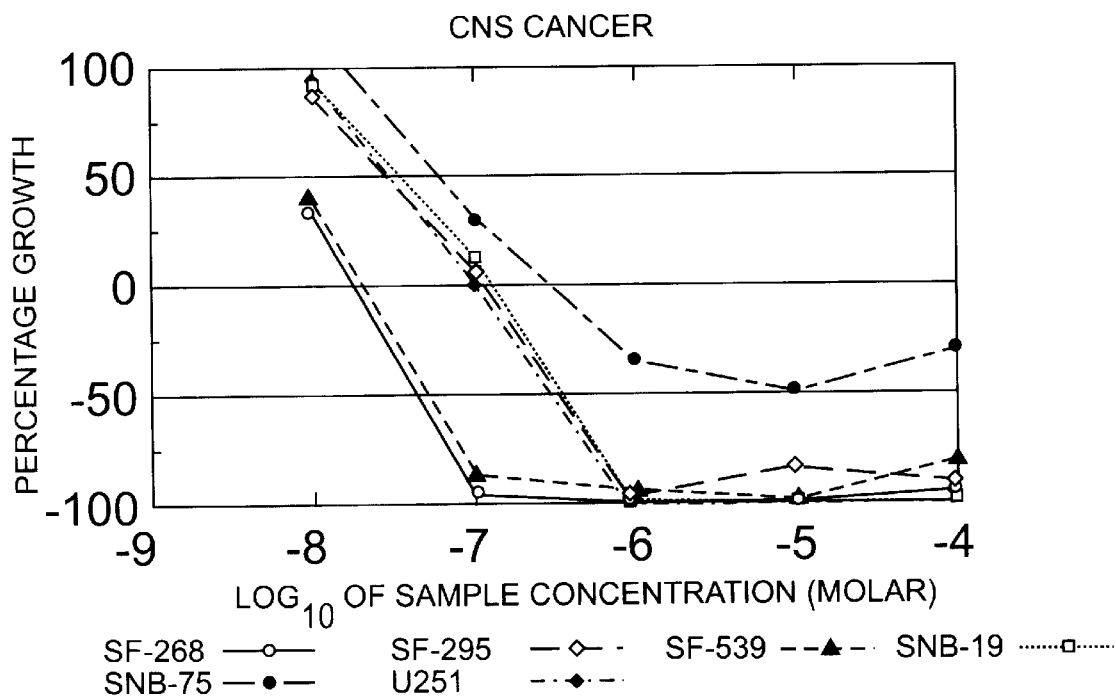
Figure 4C:
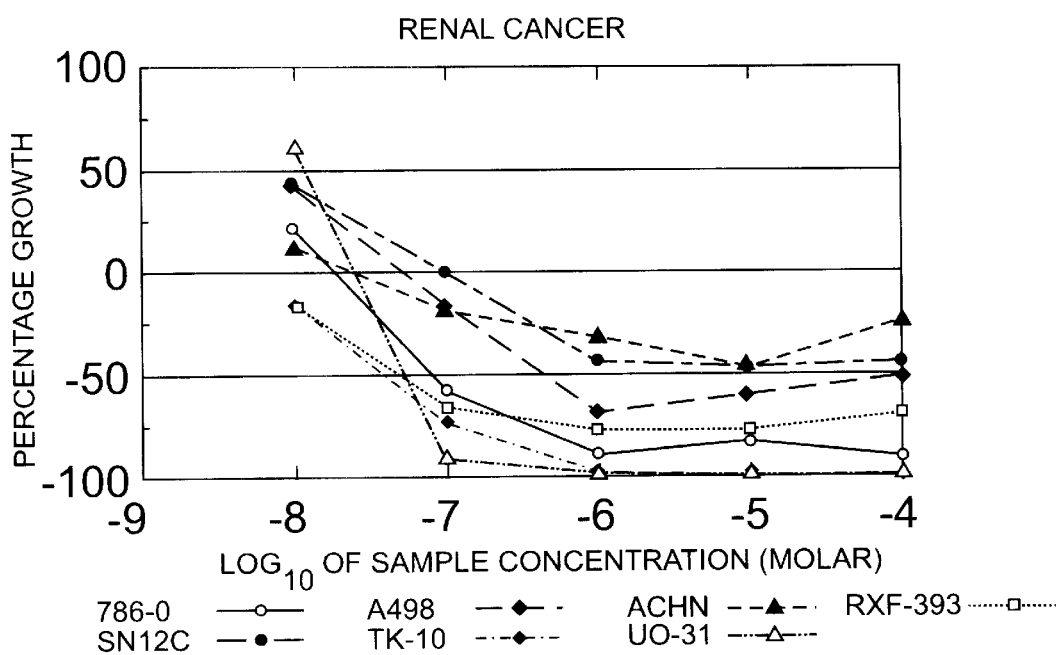
Figure 4D:
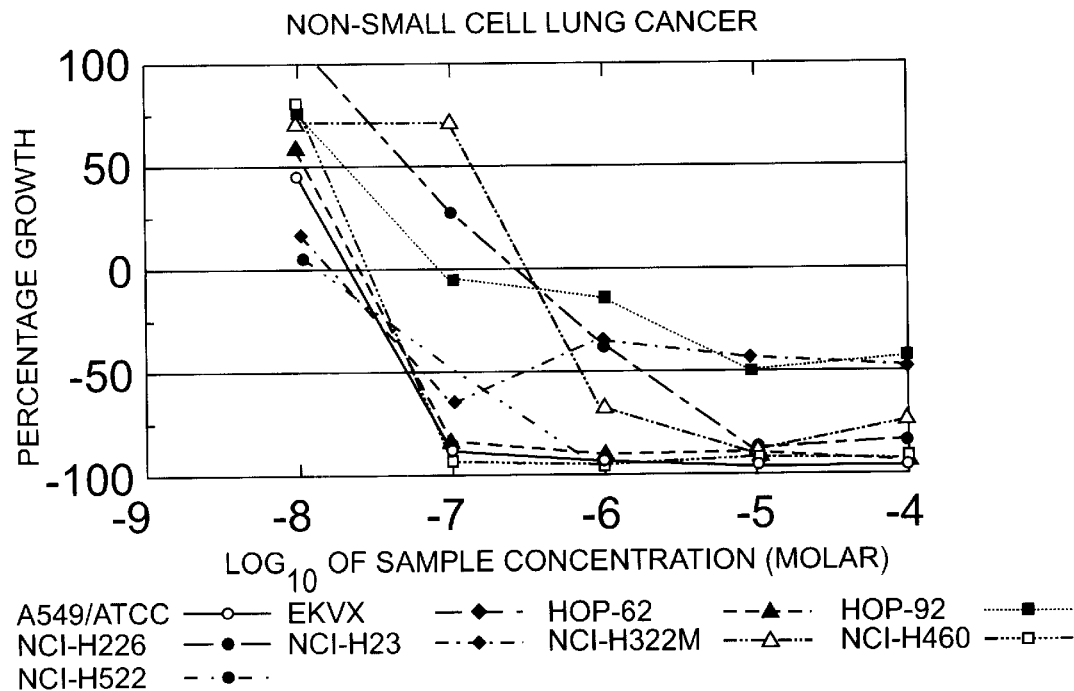
Figure 4E:
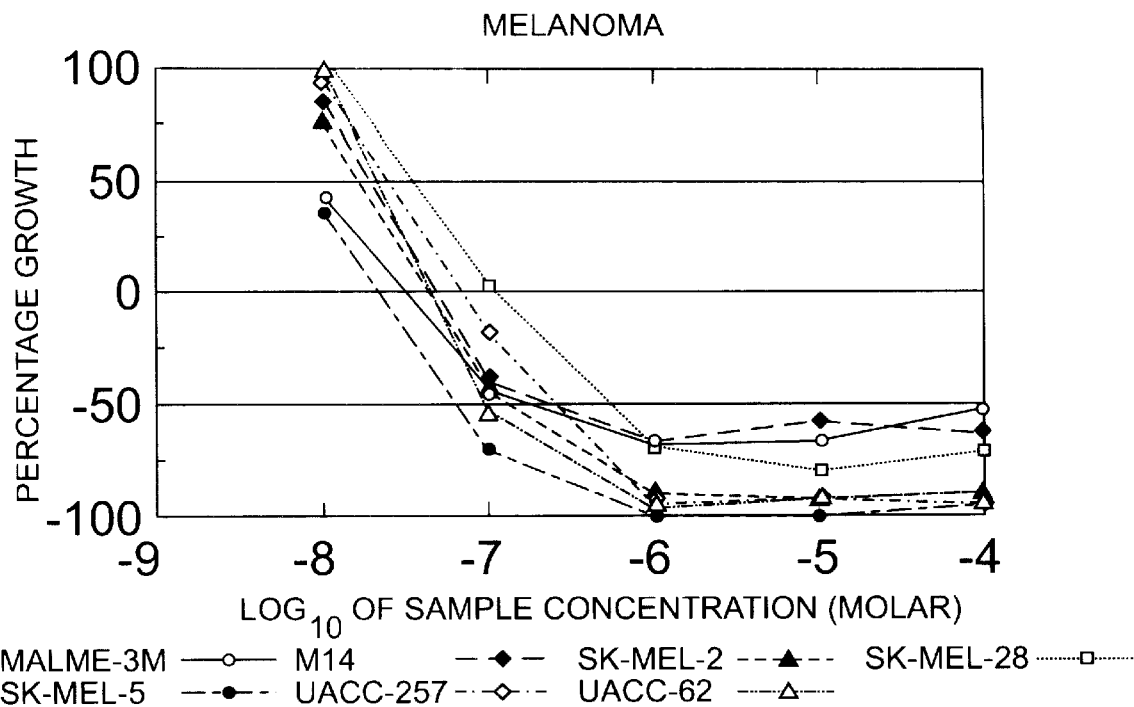
Figure 4F:
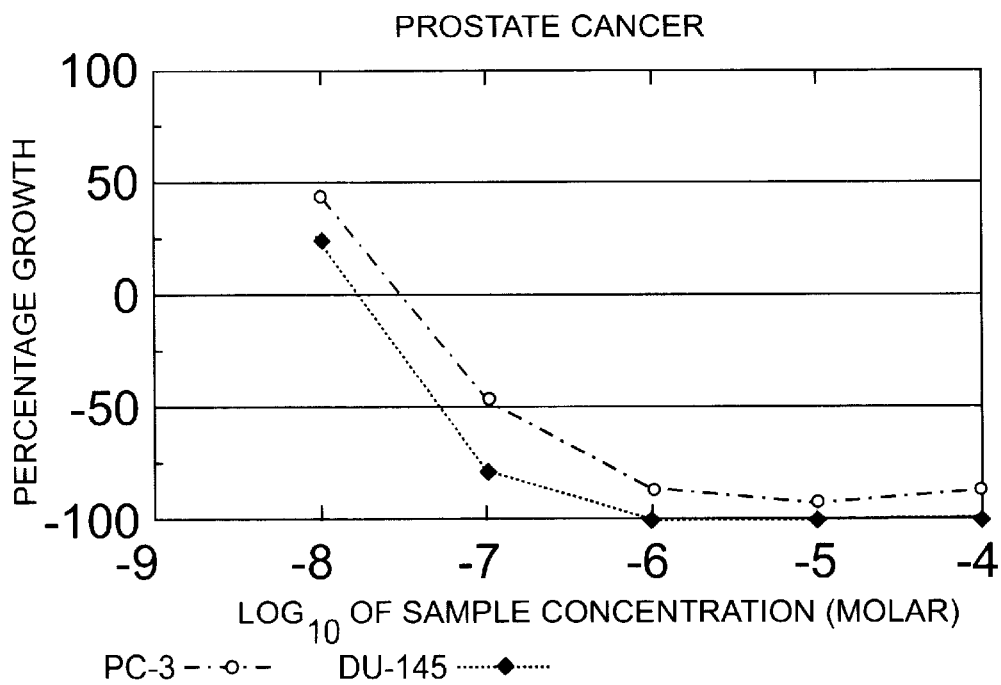
Figure 4G:
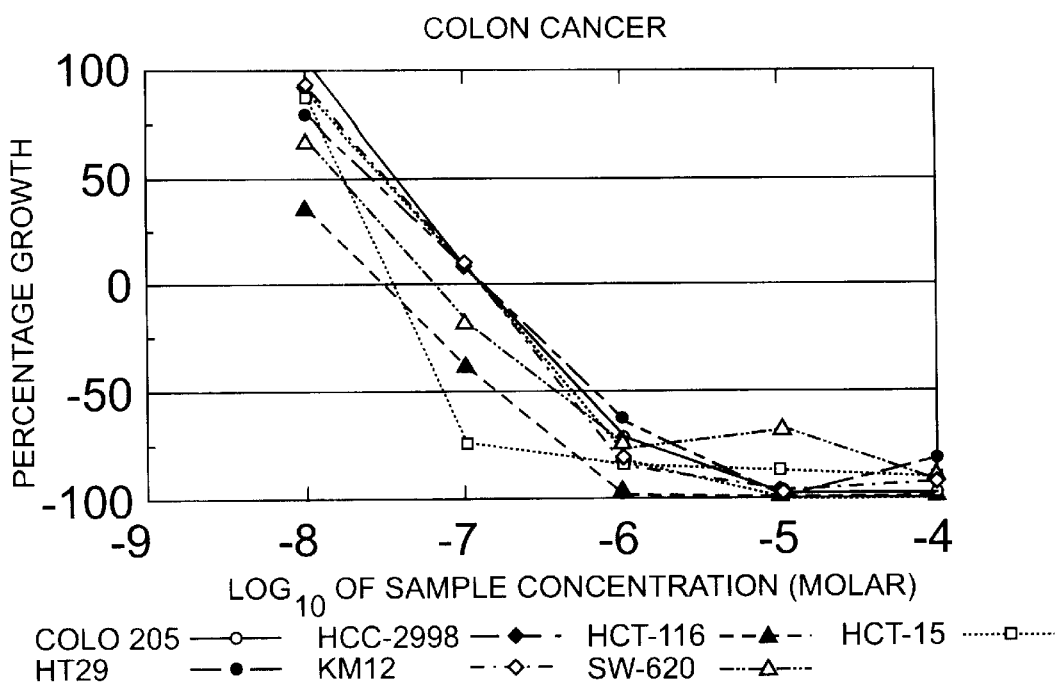
Figure 4H:
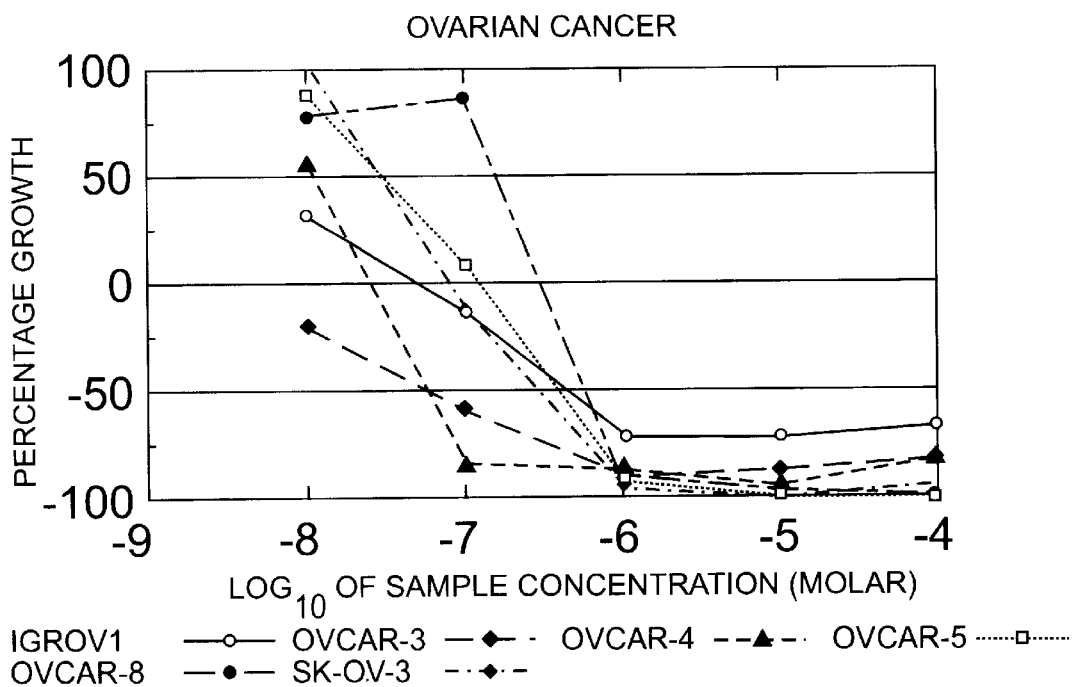
Figure 4I:
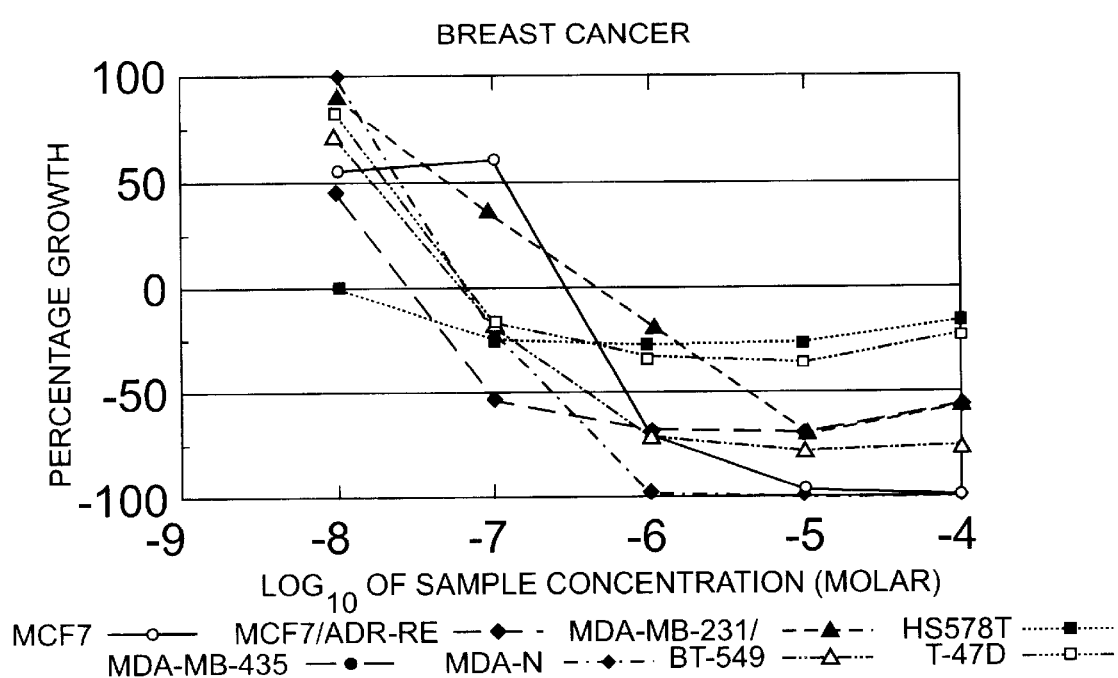
Figure 4J:
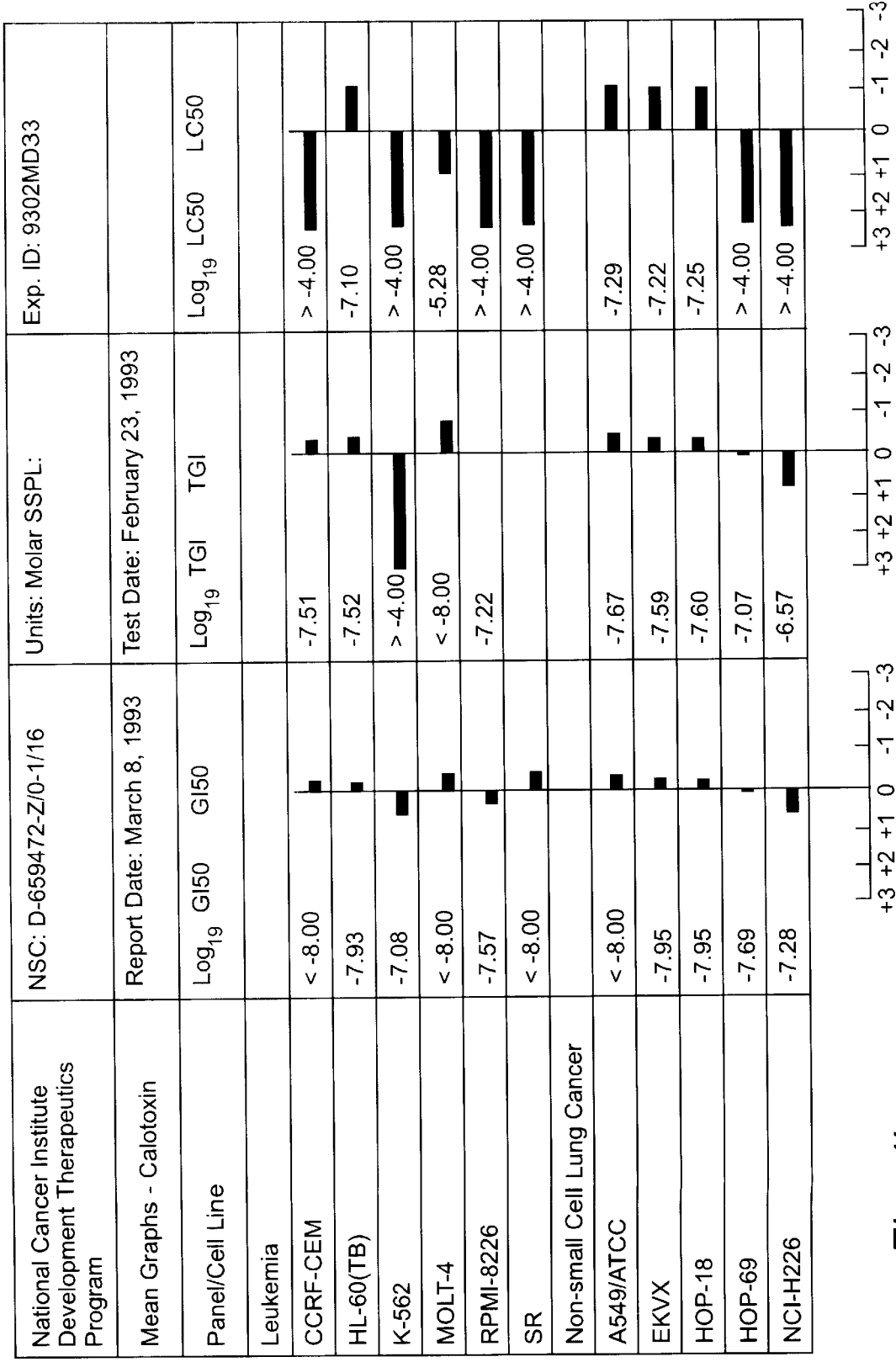
Figure 4K:
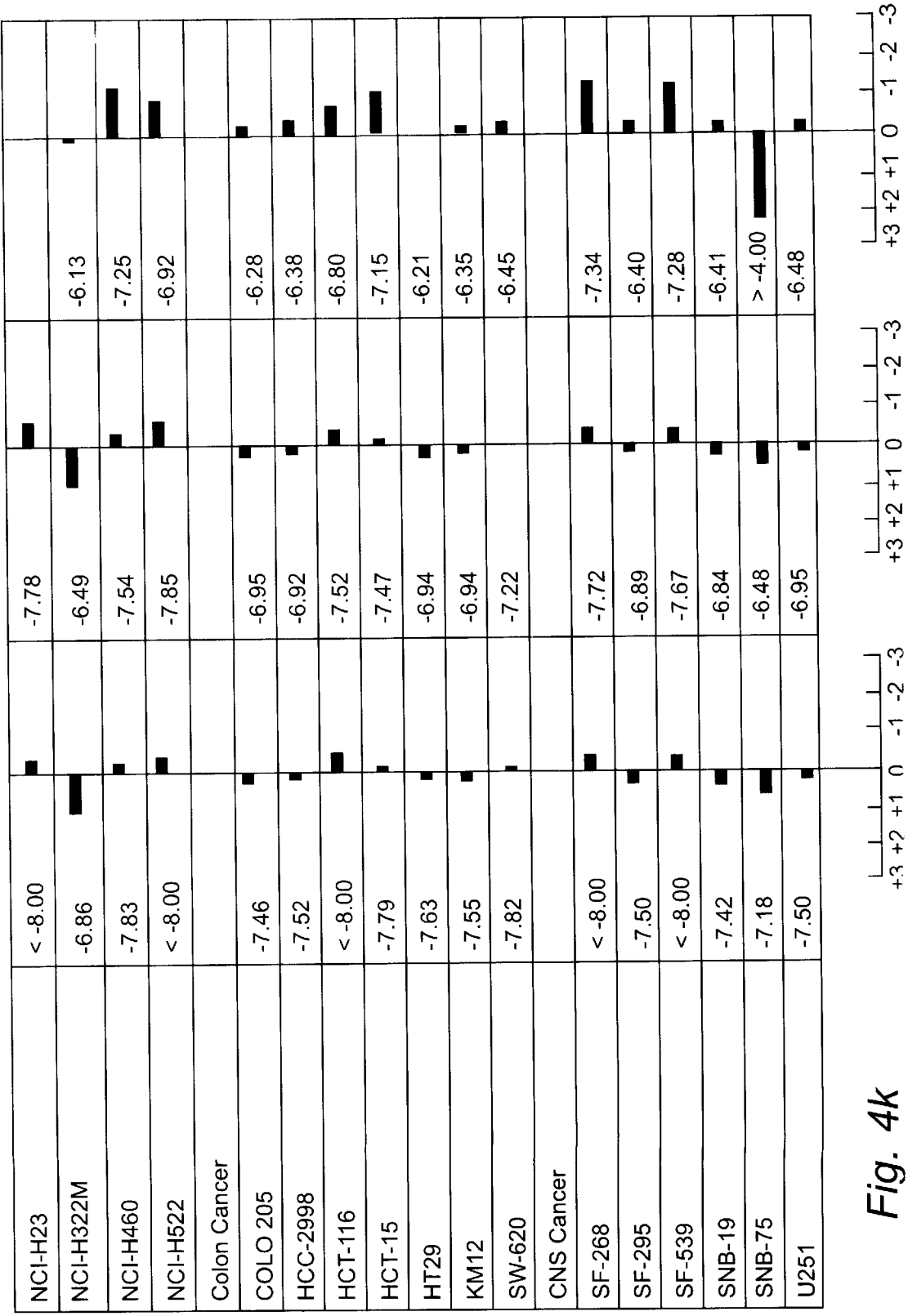
Figure 41:
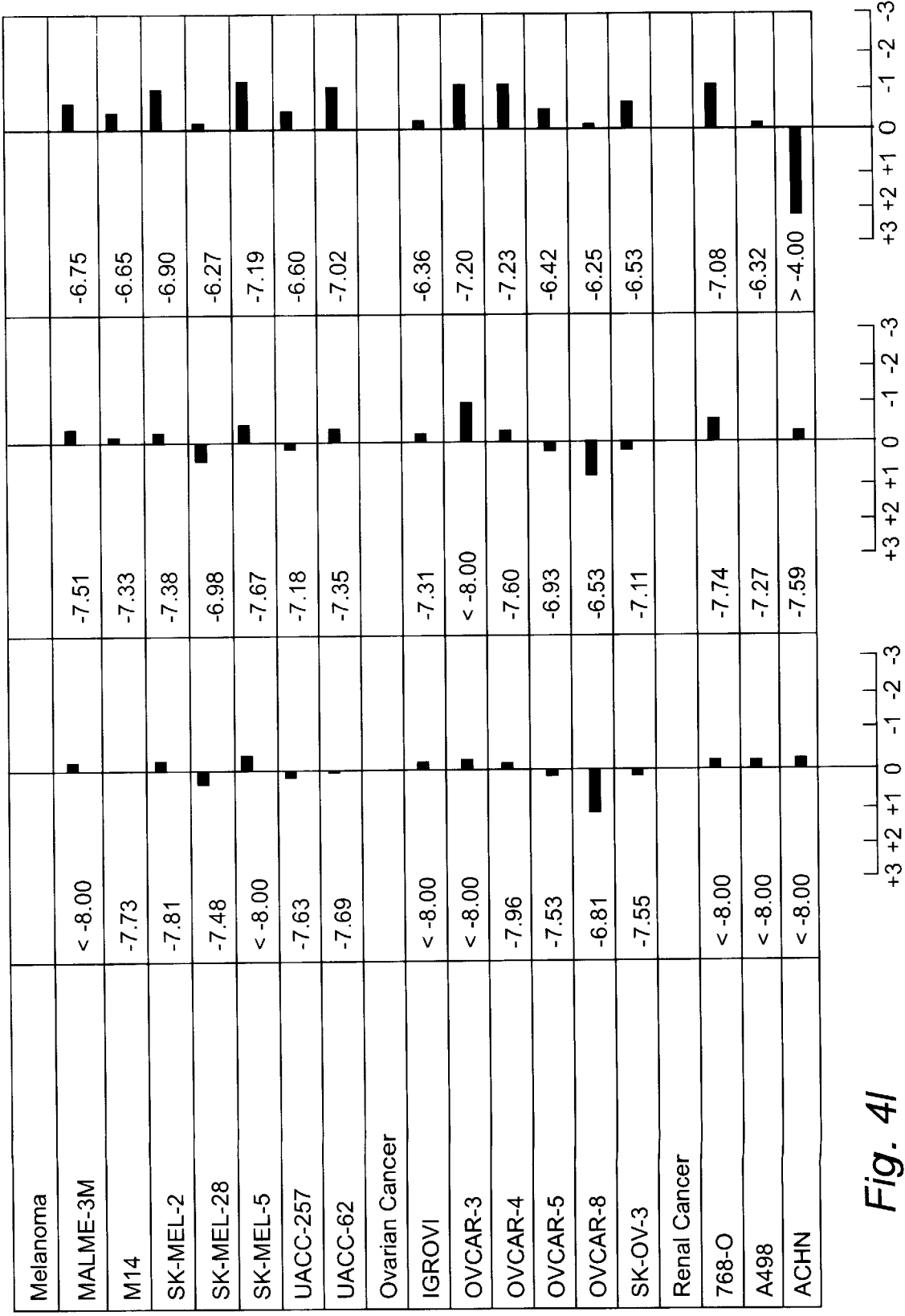
Figure 4M:
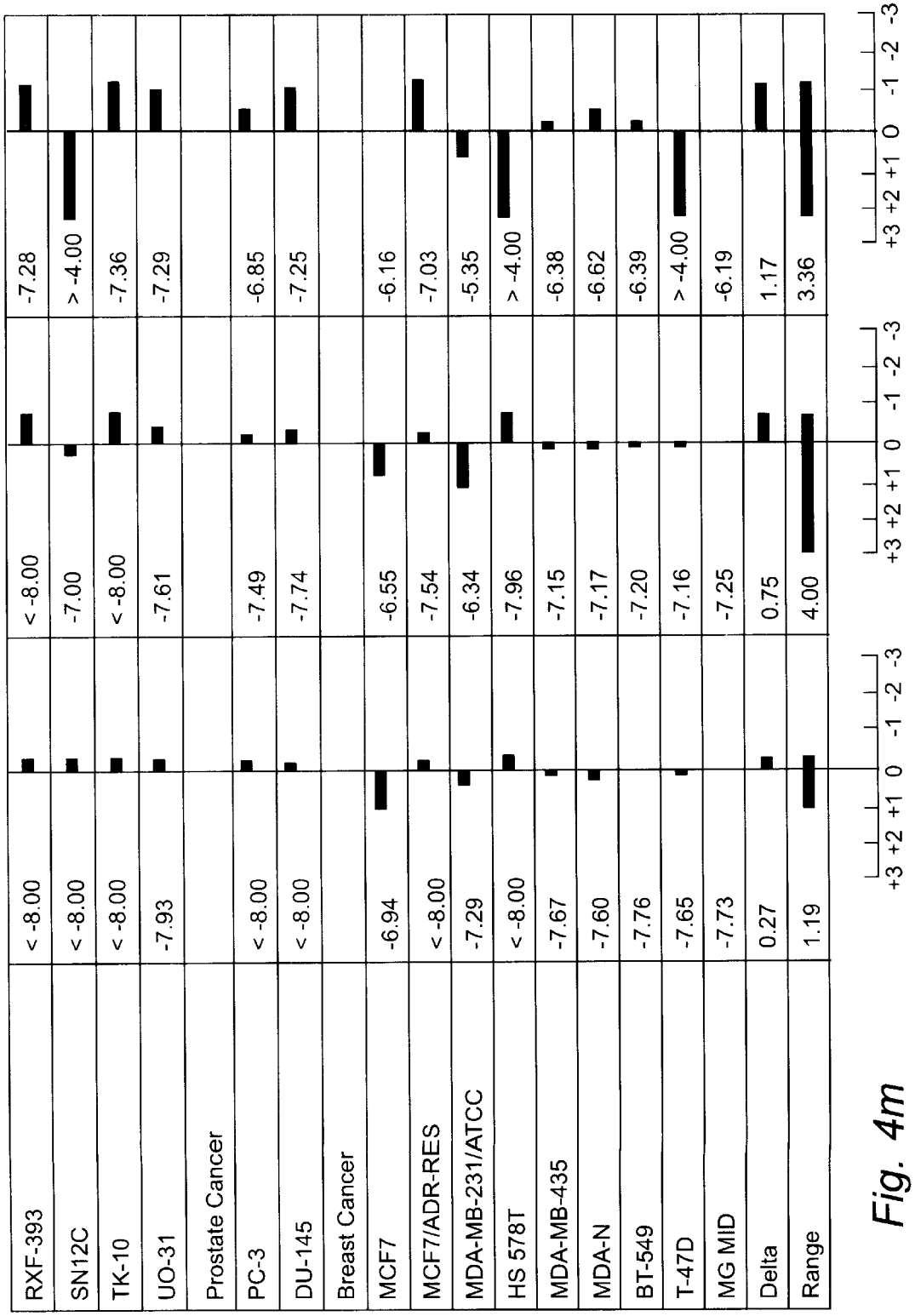

| Panel/Cell Line | Time Zero | Ctrl | Mean Optical Densities -8.0 | -7.0 | -6.0 | -5.0 | -4.0 |
|---|---|---|---|---|---|---|---|
| Leukemia | | | | | | | |
| CCRF-CEM | 0.279 | 0.993 | 0.912 | 0.166 | 0.134 | 0.134 | 0.124 |
| HL-60(TB) | 0.357 | 1.228 | 1.324 | 0.102 | 0.104 | 0.100 | 0.102 |
| K-562 | 0.120 | 0.825 | 0.904 | 0.152 | 0.085 | 0.104 | 0.111 |
| MOLT-4 | 0.490 | 1.577 | 1.463 | 0.194 | 0.163 | 0.151 | 0.337 |
| RPMI-8226 | 0.545 | 1.374 | 1.350 | 0.414 | 0.284 | 0.316 | 0.276 |
| SR | 0.348 | 1.450 | 1.279 | 0.138 | 0.127 | 0.094 | 0.150 |
| Non-Small Cell Lung Cancer | | | | | | | |
| A549/ATCC | 0.381 | 1.657 | 1.595 | 0.133 | 0.076 | 0.109 | 0.098 |
| EKVX | 1.154 | 1.728 | 1.790 | 0.617 | 0.244 | 0.352 | 0.162 |
| HOP-18 | | | | | | | |
| HOP-62 | 0.864 | 1.702 | 1.699 | 0.208 | 0.035 | 0.018 | 0.014 |
| HOP-92 | 0.636 | 0.957 | 0.970 | 0.554 | 0.269 | 0.214 | 0.173 |
| NCI-H226 | 0.919 | 1.325 | 1.367 | 0.572 | 0.199 | 0.220 | 0.093 |
| NCI-H23 | 0.516 | 1.407 | 1.201 | 0.087 | 0.080 | 0.157 | 0.250 |
| NCI-H322M | 0.564 | 1.480 | 1.519 | 0.620 | 0.461 | 0.349 | 0.273 |
| NCI-H460 | 0.177 | 1.224 | 1.181 | 0.030 | 0.013 | -0.002 | 0.018 |
| NCI-H522 | 0.476 | 0.763 | 0.729 | 0.130 | 0.044 | 0.068 | 0.098 |
| LXFL 529 | 0.456 | 1.485 | 1.493 | 0.054 | 0.018 | 0.012 | 0.015 |
| Small Cell Lung Cancer | | | | | | | |
| DMS 114 | 0.440 | 1.308 | 0.710 | 0.204 | 0.100 | 0.158 | 0.116 |
| DMS 273 | 0.256 | 1.331 | 1.342 | -0.001 | -0.012 | 0.013 | 0.016 |
| Colon Cancer | | | | | | | |
| COLO 205 | 0.277 | 1.284 | 1.215 | 0.300 | 0.087 | 0.186 | 0.091 |
| DLD-1 | 0.153 | 0.866 | 0.844 | 0.035 | 0.026 | 0.012 | 0.030 |
| HCC-2998 | 0.306 | 0.817 | 0.908 | 0.336 | 0.022 | 0.004 | 0.010 |
| HCT-116 | 0.235 | 1.376 | 1.265 | 0.094 | 0.016 | 0.031 | 0.069 |
| HCT-15 | 0.318 | 1.790 | 1.881 | 0.075 | 0.072 | 0.037 | 0.060 |
| HT29 | 0.248 | 1.271 | 1.342 | 0.221 | 0.051 | 0.046 | 0.038 |
| KM12 | | | | | | | |
| KM20L2 | 0.264 | 1.047 | 1.054 | 0.152 | 0.012 | 0.008 | 0.007 |
| SW-620 | 0.229 | 1.324 | 1.299 | 0.179 | 0.074 | 0.134 | 0.133 |
| CNS Cancer | | | | | | | |
| SF-268 | 0.496 | 1.240 | 1.109 | 0.338 | 0.049 | 0.049 | 0.093 |
| SF-295 | 0.703 | 1.521 | 1.536 | 0.409 | 0.301 | 0.171 | 0.078 |
| SF-539 | 0.846 | 1.793 | 1.702 | 0.304 | 0.061 | 0.093 | 0.113 |
| SNB-19 | 0.856 | 1.894 | 1.910 | 1.028 | 0.454 | 0.598 | 0.337 |
| SNB-75 | 0.564 | 0.864 | 0.811 | 0.572 | 0.505 | 0.414 | 0.380 |
| SNB-78 | 0.557 | 1.093 | 1.118 | 0.474 | 0.426 | 0.405 | 0.363 |
| U251 | 0.269 | 1.179 | 1.224 | 0.062 | 0.016 | 0.006 | 0.018 |
| XF 498 | 0.469 | 0.713 | 0.710 | 0.162 | 0.042 | 0.014 | 0.015 |

Fig. 1a

|  | Time |  | Log10 Concentration Mean Optical Densities | | | | |
| --- | --- | --- | --- | --- | --- | --- | --- |
| Panel/Cell Line | Zero | Ctrl | -8.0 | -7.0 | -6.0 | -5.0 | -4.0 |
| Melanoma | | | | | | | |
| LOX IMVI | 0.256 | 1.365 | 1.346 | 0.016 | -0.001 | 0.017 | 0.016 |
| MALME-3M | 0.644 | 1.259 | 1.255 | 0.235 | 0.124 | 0.066 | 0.069 |
| M14 | 0.333 | 1.167 | 1.160 | 0.240 | 0.038 | 0.035 | 0.004 |
| M19-MEL | 0.284 | 1.126 | 1.124 | 0.386 | 0.094 | 0.144 | 0.146 |
| SK-MEL-2 | 0.570 | 1.357 | 1.322 | 0.280 | 0.091 | 0.078 | 0.075 |
| SK-MEL-28 | 0.254 | 0.562 | 0.608 | 0.278 | 0.198 | 0.170 | 0.093 |
| SK-MEL-5 | 0.485 | 1.905 | 1.896 | 0.249 | 0.200 | 0.179 | 0.134 |
| UACC-257 | 0.734 | 2.040 | 2.117 | 0.872 | 0.483 | 0.463 | 0.344 |
| UACC-62 | 0.516 | 1.714 | 1.649 | 0.465 | 0.103 | 0.163 | 0.095 |
| Ovarian Cancer | | | | | | | |
| IGROV1 | 0.444 | 1.377 | 1.422 | 0.510 | 0.257 | 0.302 | 0.320 |
| OVCAR-3 | 0.654 | 1.189 | 1.238 | 0.280 | 0.324 | 0.296 | 0.257 |
| OVCAR-4 | 0.417 | 1.051 | 0.974 | 0.048 | 0.011 | 0.005 | 0.004 |
| OVCAR-5 | 0.346 | 0.848 | 0.852 | 0.043 | 0.017 | -0.008 | 0.012 |
| OVCAR-8 | 0.615 | 1.784 | 1.799 | 0.530 | 0.092 | 0.065 | 0.206 |
| SK-OV-3 | 0.485 | 1.165 | 1.097 | 0.480 | 0.172 | 0.251 | 0.122 |
| Renal Cancer | | | | | | | |
| 786-0 | 0.274 | 1.093 | 1.062 | 0.027 | 0.011 | 0.008 | 0.027 |
| A498 | 0.618 | 1.360 | 1.348 | 0.872 | 0.718 | 0.544 | 0.341 |
| ACHN | 0.412 | 1.349 | 1.204 | 0.130 | 0.024 | 0.020 | 0.069 |
| CAKI-1 | | | | | | | |
| RXF-393 | 0.856 | 1.266 | 1.203 | 0.613 | 0.391 | 0.499 | 0.668 |
| RXF-631 | | | | | | | |
| SN12C | 0.239 | 1.533 | 1.531 | 0.022 | 0.036 | 0.020 | 0.040 |
| TK-10 | 0.650 | 1.057 | 1.064 | 0.227 | 0.042 | 0.060 | 0.088 |
| UO-31 | 0.789 | 1.347 | 1.424 | 0.715 | 0.462 | 0.466 | 0.607 |

*Fig. 1b*

| Panel/Cell Line | Log10 Concentration Percent Growth | | | | | GI50 | TGI | LC50 |
|---|---|---|---|---|---|---|---|---|
| | -8.0 | -7.0 | -6.0 | -5.0 | -4.0 | | | |
| Leukemia | | | | | | | | |
| CCRF-CEM | 89 | -41 | -52 | -52 | -56 | 1.99E-08 | 4.86E-08 | 6.73E-07 |
| HL-60(TB) | 111 | -71 | -71 | -72 | -71 | 2.16E-08 | 4.06E-08 | 7.63E-08 |
| K-562 | 111 | 4 | -30 | -13 | -7 | 3.74E-08 | 1.35E-07 | >1.00E-04 |
| MOLT-4 | 90 | -60 | -67 | -69 | -31 | 1.83E-08 | 3.95E-08 | |
| RPMI-8226 | 97 | -24 | -48 | -42 | -49 | 2.45E-08 | 6.34E-08 | >1.00E-04 |
| SR | 84 | -60 | -64 | -73 | -57 | 1.73E-08 | 3.83E-08 | 8.48E-08 |
| Non-Small Cell Lung Cancer | | | | | | | | |
| A549/ATCC | 95 | -65 | -80 | -71 | -74 | 1.91E-08 | 3.92E-08 | 8.04E-08 |
| EKVX | 111 | -47 | -79 | -70 | -86 | 2.43E-08 | 5.06E-08 | 1.28E-07 |
| HOP-18 | | | | | | | | |
| HOP-62 | 100 | -76 | -96 | -98 | -98 | 1.92E-08 | 3.70E-08 | 7.12E-08 |
| HOP-92 | 104 | -13 | -58 | -66 | -73 | 2.89E-08 | 7.75E-08 | 6.75E-07 |
| NCI-H226 | 110 | -38 | -78 | -76 | -90 | 2.56E-08 | 5.57E-08 | 2.01E-07 |
| NCI-H23 | 77 | -83 | -84 | -70 | -52 | 1.47E-08 | 3.02E-08 | 6.21E-08 |
| NCI-H322M | 104 | 6 | -18 | -38 | -52 | 3.57E-08 | 1.79E-07 | 7.60E-05 |
| NCI-H460 | 96 | -83 | -93 | -100 | -90 | 1.80E-08 | 3.43E-08 | 6.52E-08 |
| NCI-H522 | 88 | -73 | -91 | -86 | -80 | 1.73E-08 | 3.53E-08 | 7.23E-08 |
| LXFL 529 | 101 | -88 | -96 | -97 | -97 | 1.86E-08 | 3.41E-08 | 6.27E-08 |
| Small Cell Lung Cancer | | | | | | | | |
| DMS 114 | 31 | . | -77 | -64 | -74 | <1.00E-08 | 3.74E-08 | 3.12E-07 |
| DMS 273 | 101 | -100 | -100 | -95 | -94 | 1.79E-08 | 3.18E-08 | 5.64E-08 |
| Colon Cancer | | | | | | | | |
| COLO 205 | 93 | 2 | -69 | -32 | -67 | 2.98E-08 | 1.08E-07 | . |
| DLD-1 | 97 | -77 | -83 | -92 | -80 | 1.86E-08 | 3.59E-08 | 6.96E-08 |
| HCC-2998 | 118 | 6 | -93 | -99 | -97 | 4.03E-08 | 1.15E-07 | 3.68E-07 |
| HCT-116 | 90 | -60 | -93 | -87 | -71 | 1.85E-08 | 3.98E-08 | 8.55E-08 |
| HCT-15 | 106 | -77 | -77 | -88 | -81 | 2.03E-08 | 3.81E-08 | 7.16E-08 |

Fig. 1c

| Panel/Cell Line | Log10 Concentration Percent Growth | | | | | | GI50 | TGI LC50 | |
|---|---|---|---|---|---|---|---|---|---|
| | -8.0 | -7.0 | -6.0 | -5.0 | -4.0 | | | | |
| Colon Cancer | | | | | | | | | |
| HT29 | 107 | -11 | -80 | -81 | -84 | | 3.03E-08 | 8.05E-08 | 3.70E-07 |
| KM12 | | | | | | | | | |
| KM20L2 | 101 | -43 | -95 | -97 | -97 | | 2.27E-08 | 5.05E-08 | 1.38E-07 |
| SW-620 | 98 | -22 | -68 | -41 | -42 | | 2.51E-08 | 6.57E-08 | . |
| CNS Cancer | | | | | | | | | |
| SF-268 | 82 | -32 | -90 | -90 | -81 | | 1.92E-08 | 5.27E-08 | 2.06E-07 |
| SF-295 | 102 | -42 | -57 | -76 | -89 | | 2.30E-08 | 5.12E-08 | 3.39E-07 |
| SF-539 | 90 | -64 | -93 | -89 | -87 | | 1.83E-08 | 3.85E-08 | 8.11E-08 |
| SNB-19 | 102 | 16 | -47 | -30 | -61 | | 4.03E-08 | 1.81E-07 | 4.43E-05 |
| SNB-75 | 82 | 3 | -10 | -27 | -33 | | 2.53E-08 | 1.60E-07 | >1.00E-04 |
| SNB-78 | 105 | -15 | -24 | -27 | -35 | | 2.86E-08 | 7.50E-08 | >1.00E-04 |
| U251 | 105 | -77 | -94 | -96 | -93 | | 2.00E-08 | 3.78E-08 | 7.11E-08 |
| XF 498 | 99 | -66 | -91 | -97 | -97 | | 1.98E-08 | 3.99E-08 | 8.04E-08 |
| Melanoma | | | | | | | | | |
| LOX IMVI | 98 | -94 | -100 | -94 | -94 | | 1.78E-08 | 3.25E-08 | 5.91E-08 |
| MALME-3M | 99 | -64 | . | -90 | -89 | | 2.01E-08 | 4.08E-08 | 8.26E-08 |
| M14 | 99 | -28 | -89 | -90 | -99 | | 2.44E-08 | 6.03E-08 | 2.31E-07 |
| M19-MEL | 100 | 12 | -67 | -49 | -49 | | 3.69E-08 | 1.42E-07 | . |
| SK-MEL-2 | 96 | -51 | -84 | -86 | -87 | | 2.05E-08 | 4.50E-08 | 9.88E-08 |
| SK-MEL-28 | 115 | 8 | -22 | -33 | -64 | | 4.03E-08 | 1.80E-07 | 3.56E-05 |
| SK-MEL-5 | 99 | -49 | -59 | -63 | -72 | | 2.16E-08 | 4.69E-06 | 1.36E-07 |
| UACC-257 | 106 | 11 | -34 | -37 | -53 | | 3.86E-08 | 1.72E-07 | 6.40E-05 |
| UACC-62 | 95 | -10 | -80 | -68 | -82 | | 2.67E-08 | 8.04E-08 | 3.73E-07 |
| Ovarian Cancer | | | | | | | | | |
| IGROV1 | 105 | 7 | -42 | -32 | -28 | | 3.63E-08 | 1.39E-07 | >1.00E-04 |
| OVCAR-3 | 109 | -57 | -51 | -55 | -61 | | 2.27E-08 | 4.53E-08 | 9.05E-08 |
| OVCAR-4 | 88 | -88 | -97 | -99 | -99 | | 1.64E-08 | 3.15E-08 | 6.05E-08 |

Fig. 1d

| Panel/Cell Line | Log10 Concentration Percent Growth | | | | | GI50 | TGI | LC50 |
|---|---|---|---|---|---|---|---|---|
| | -8.0 | -7.0 | -6.0 | -5.0 | -4.0 | | | |
| Ovarian Cancer | | | | | | | | |
| OVCAR-5 | 101 | -88 | -95 | 100 | -97 | 1.86E-08 | 3.42E-08 | 6.31E-08 |
| OVCAR-8 | 101 | -14 | -85 | -90 | -67 | 2.79E-08 | 7.60E-08 | 3.22E-07 |
| SK-OV-3 | 90 | -1 | -64 | -48 | . | 2.75E-08 | 9.72E-08 | |
| Renal Cancer | | | | | | | | |
| 786-0 | 96 | -90 | -96 | -97 | -90 | 1.77E-08 | 3.28E-08 | 6.09E-06 |
| A498 | 98 | 34 | 13 | -12 | -45 | 5.66E-08 | 3.38E-06 | >1.00E-04 |
| ACHN | 85 | -68 | -94 | -95 | -83 | 1.68E-08 | 3.57E-08 | 7.56E-08 |
| CAKI-1 | | | | | | | | |
| RXF-393 | 84 | -28 | -54 | -42 | -22 | 2.02E-08 | 5.61E-08 | |
| RXF-631 | | | | | | | | |
| SN12C | 100 | -91 | -85 | -92 | -83 | 1.83E-08 | 3.34E-08 | 6.11E-08 |
| TK-10 | 102 | . | -94 | -91 | -86 | 3.38E-08 | 1.10E-07 | 3.58E-07 |
| UO-31 | 114 | -9 | -41 | -41 | -23 | 3.30E-08 | 8.40E-08 | >1.00E-04 |

Fig. 1e

PHARMACEUTICAL COMPOSITION CONTAINING USCHARIDIN OR ITS ANALOGUES

This invention relates to a composition comprising the cardenolide glycoside uscharin.

Plants of the family Asclepidaceae are known to be extremely poisonous. Such plants have a history of use in folk medicines in those areas where they occur naturally, for example in South East Asia and Africa. Two of the best known representatives of the Asclepiadaceae are *Calotropis gigantea* and *Calotropis procera*. Extracts from *Calotropis procera* plants have traditionally been used as an abortifacient, for infanticide, for rheumatic pain and to produce a purgative.

The stems, flowers and leaves of plants from the family Asclepiadaceae (including *Calotropis gigantea* and *Calotropis procera*) are known to contain certain compounds known as cardenolides. In several species substantial amounts of cardenolides have been found to be concentrated in the latex (Roeske et al, in Biochemical Interactions Between Plants and Insects published in Volume 10 of Recent Advances in Phytochemistry, Plenum Press, New York (ed. Wallace), Seiber et al, Phytochemistry 21:2343 (1982), Seiber et al, in Isopentoids in Plants, Academic Press (ed Nes, 1984) and Seiber et al, in J. Chem. Ecol. 6:321 (1980)). The natural production of carcenolides in *Ascelopias curassavia* has been reported by Groeneveld et al in Phytochemistry 29(11):3479–3438 (1990). Examples of carcenolide glycosides found in *C. procera* are voruscharin, uscharin, uscharidin, calotropin, calactin, calotoxin, and caletropagenin Formula I shows the chemical structure of these carcenolides.

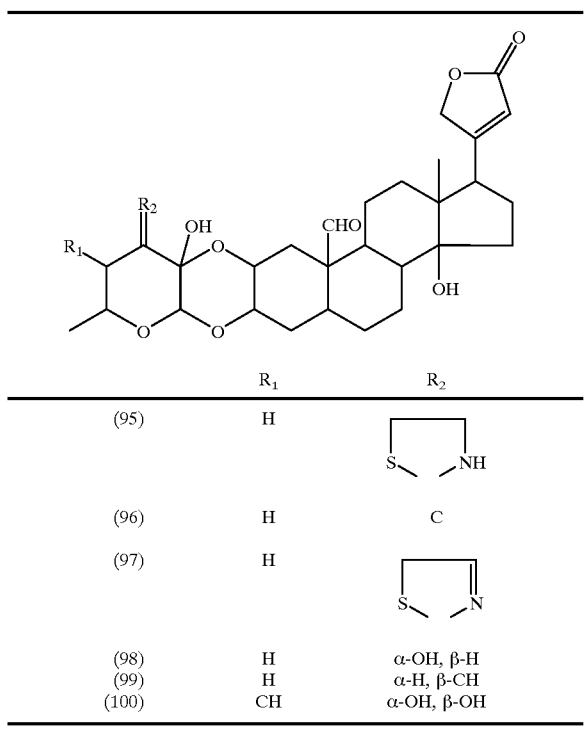

| | $R_1$ | $R_2$ |
|---|---|---|
| (95) | H | S⌐NH |
| (96) | H | C |
| (97) | H | S⌐N |
| (98) | H | α-OH, β-H |
| (99) | H | α-H, β-CH |
| (100) | CH | α-OH, β-OH |

It has now been found that the cardenolide uscharin is particularly useful for medical purposes. Whilst uscharin has been isolated and its chemical structure determined, no utility for this compound has previously been reported.

The present invention thus provides a composition comprising uscharin, the analogues and salts thereof as active ingredient together with a pharmaceutically acceptable carrier or excipient.

Further, the present invention also provides the use of uscharin, the analogues and salts thereof for medical (including veterinary) purposes.

Previously, certain cardenolide glycosides such as calotropin and uzarigenin have been noted to have cytotoxic activity against primate tumour cells. Certain cardenolide glycosides from the Asclepiadaceae family share structural and pharmacological similarities with the Digitalis cardiac glycosides. Whilst we do not wish to be bound by theoretical considerations it is believed that the cytotoxicity of some cardenolide glycosides is related to the inhibition of the plasma membrane bound $Na^+/K^+$ ATPase (ie analogous to the manner in which Digitalis cardiac glycosides exert their toxic effects). However, it has also been shown that whilst some cardenolide glycosides are cytotoxic to cell cultures they have no in vivo tumour-inhibiting activity. This is true of calotropin and uzarigenin.

It has never previously been proposed that uscharin would be useful for medical applications. The inventors' results have shown that at 1 mg/ml a primary extract of *Calotropis gigantea* known as CGE-1 does have tumour inhibiting activity in rats (weighing about 200 g) and does not lead to the death of the test animals.

Typically, the use of uscharin according to the present invention is to combat cell proliferation for example in the treatment of cancer, Thus administration of uscharin may kill or reduce the growth rate of cancer cells and may also be of application in other medical conditions presenting symptoms of excessive or uncontrolled cell proliferation.

The word "combat" is used herein to refer to treatment of an existing condition so as to alleviate or reverse the symptoms of the condition in an affected human or animal and to prevent such a condition in a healthy human or animal.

The composition according to the present invention may be administered by any convenient route and mention may be made of enteral, parenteral, topical administration and the composition will be formulated accordingly. Conveniently, the composition may be administered locally to the affected site, generally by means of injection. Thus the uscharin will be suitably dissolved and/or suspended in a pharmaceutically acceptable liquid carrier medium, which will generally be aqueous-based, for example an isotonic solution. Alternatively, the composition according to the invention may be taken orally.

Formulations for parenteral administration include aqueous and non-aqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemoraneous injection solutions and suspensions may be prepared from sterile powders, granules and tablets of the kind previously described.

The dose will depend on a number of factors known to the skilled physician including the severity of the conditions, the identity of the recipient; and also the is efficacy and toxicity of the particular composition which is being administered. Generally doses in the range 0.1–100 mg/kg body weight may be used, particularly 1–10 mg/kg. The frequency of administration will vary depending on the rate of metabolism or excretion of the administered compound, but may be repeated daily, optionally as two or more sub-doses. Unit doses of 20 to 500 mg, preferably 100 to 400 mg may be used.

A single dosage may be given daily or smaller quantities or dosage units may be given at intervals throughout a 24 hour period, for example dosage units given 2, 3 or 4 times throughout the day.

Any type of cancer or condition involving cell proliferation may be treated by the present invention. Uscharin is especially useful for the treatment of cancers such as leukaemia, non-small cell lung cancer, small cell lung cancer, colon cancer, CNS cancer, melanoma, ovarian cancer, renal cancer, prostrate cancer, and breast cancer. However the invention is not limited to treatment of these specific conditions since uscharin is believed to be of general effect.

Cancers where uscharin is particularly efficacious include ovarian cancer and skin cancer.

Uscharin may by produced by any convenient method, for example by chemical synthesis. Alternatively the uscharin may be conveniently extracted and purified from organisms (for example plants of the family Asclepiadacaeae) which produce uscharin naturally. It is also envisaged that uscharin may be manufactured using genetically engineered micro-organisms, plants or animals or may be made using cell-culture or other biotechnological techniques.

Further, the present invention also provides the use of a composition as described above for medical purposes, for example to combat conditions in which cell proliferation is undesirable (eg cancer).

In another aspect, the present invention provides the use of uscharin in the manufacture of a medicament. Generally such medicament would be of use to combat cancer and other conditions where cell proliferation is undesirable.

In a further aspect, the present invention provides a method of treatment of a human or non-human animal body, said method comprising administering to said body a composition as described above.

The present invention is now further described by means of the following, non-limiting Examples.

EXAMPLE 1

Preparation of Uscharin Extract
(i) Isolation of CGE-1

Leaves of Calotropis gigantea (500 g) were Soxhlet extracted initially with petroleum ether (60–80), then ethyl acetate and finally methanol. The cell culture bioassays showed that the ethyl acetate fraction contained cytotoxic activity. The ethyl acetate extract was subjected to vacuum liquid chromatography (VLC) on silica gel 60H (Merck). Elution was initiated with petroleum ether (60–80) and proceeded with petroleum ether containing progressively greater amounts of ethyl acetate through to ethyl acetate only. Elution was then continued with ethyl acetate containing progressively greater amounts of methanol.

Samples of the traction were collected and prepared for cytotoxicity testing by solubilisation in 0.1% Tween.

The greatest cytotoxic activity ($ED_{50}$<0.10 µg/ml) was found in the 70–80 ethyl acetate in petroleum ether fractions. The cytotoxic compound CGE-1 (72.0 mg) ($ED_{50}$<0.09 µg/ml) was isolated as a white semi-crystalline precipitate from this fraction.

(ii) Isolation of CGE-2

Another less cytotoxic compound, CGE-2 (101.0 mg) ($ED_{50}$<8.0 µg/ml) was isolated from the 100% ethyl acetate fraction as a semi-crystalline precipitate.

(iii) Properties of CGE-1

White powder, found 587.2511, $C_{31}H_{41}NO_8S$ requires 587,2553. $[\alpha]_0$+10.0° (c.0.1,$CH_3OH_4$) IR $V_{max}$ $CM^{-1}$: 3465, 2960, 2920, 2840, 2720, 1735, 1730, 1705, 1625, 1540, 1160, 1110, 1060, 1040. EIMS m/z (rel. int.) 587 [M+] (4.0), 233 (14.9), 215 (8.6), 187 (9.8), 183

Activity of CGE-1

At a concentration of 1 mg/ml, CGE-1 has d tumor inhibiting activity in rats weighing approximately 200 g and does not lead to the death of the rat.

CGE-1 was found to contain Uscharin

Example 2

Isolation of Uscharin from Calotropis gigantea leaves.
Extraction

The plant material was minced to a fine powder in a bench grinder. The powder was extracted in a Soxhlet with petroleum ether (60–80) and the ethyl acetate, until exhaustion. The ethyl acetate traction was concentrated to dryness using a rotary evaporator.
Fractionation Vacuum Liquid Chromatography was used for the initial fractionation of the crude extract Silica gel 60H (Merck) was packed in a scintered funnel under vacuum to give a compact column. The crude extract, adsorbed in silica, was applied to the column. Elution was initiated with petroleum ether and proceeded with petroleum ether containing progressively greater amounts of ethyl acetate than with ethyl acetate through to methanol. The fractions were concentrated using a rotary evaporator. 10 mg of each fraction were prepared for cytotoxicity testing (see MTT assay for method) by solubilisation in DMSO. The fraction containing the greatest cytotoxic activity was subjected to a sephadex column to remove any remaining chlorophyll.
Sephadex Column The fraction was dissolved in a minimum volume of chloroform and applied to a column containing lipophilic sephadex LH-20 (Sigma) which had been packed in chloroform. Elution was with chloroform, chloroform with methanol and methanol. As before fraction were dried and tested for activity. The fraction with the greatest activity was further fractionated with a silica gel column.
Silica Gel Column The fraction was dissolved in a minimum volume of chloroform and applied to a column containing silica gel (packed in chloroform). Elution was with chloroform, chloroform with methanol and methanol. This column yielded a fraction of almost pure uscharin. The pure compound was obtained from this fraction by preparative TLC.
Preparative TLC The fraction was spotted onto glass silica gel plates. The plates were run in ethyl acetate and methanol (97:3). The silica was scratched from the plate and the uscharin eluted with ethyl acetate.

Once the compound had been isolated, its identity was confirmed by spectroscopic techniques.

EXAMPLE 3

Cytotoxicity Bioassay of Uscharin

Cytotoxicity bioassays were performed. The cell line used was a human ovarian small cell carcinoma SCC Wm 1(151) which was grown as a monolayer in Dulbecco's Modified Eagles Medium (Gibco) supplemented with 5% foetal calf serum (v/v), sodium pyruvate (1 mM), penicillin (50 IU/ml) and streptomycin (50 μg/ml). Cultures were maintained in a humidified atmosphere of 5% $CO_2$/95% air at 37°.

Single cell suspensions were obtained by trypsinisation of the monolayer cultures and an equal number of cells ($10^3$–$10^4$ depending on the cell line) was inoculated into each 33 $mm^2$ well of a 96 well plate in 190 μl of culture medium. The plates were incubated for 24 hours to allow cells to adhere. At this point 10 μl of an appropriate concentration of plant extract or control solvent was added to each well. The cells were exposed to the drug for 3 days after which the medium was removed, the monolayers washed with PBS and fresh medium added. This was repeated 24 hours later. Following a further 24 hours incubation 100 μg (50 μl of 2 mg/ml in PBS) MTT (3-(4,5 dimethylthiazol-2-yl)-2,5-diphenyltetrazolium bromide) was added to each well and the cells were incubated at 37° C. for 4 hours. Plates were then processed using a modified version (Carmichael et al, 1987) of the assay first described by Mossman, T.(1983), where DMSO was used in preference to acid isopropanol to solubilise the formazan crystals. The contents of each well were mixed and the plate was read immediately at 540 nm on a Flow Titertek Multiscan MCC/340 Mk 11 plate reader. Cells were set up in parallel at two densities, $10^3$ and $2\times10^3$ cells/well, and the results from an assay were discarded if the ratio of the OD readings of the two densities was greater than 2.25:1 or less than 1.75:1.

The results obtained were as shown in FIG. 1

EXAMPLE 4
In vitro Screening of Uscharin

Uscharin was obtained as in Example 2 and was subjected to in vitro cell screening at the National Cancer Institute (NCI), USA in respect of a panel of cancel cell types organised into subpanels representing leukemia, lung cancers, colon cancer, cancer of the central nervous system, melanoma, ovarian cancer, renal cancer, and in some cases prostate cancer and breast cancer also.

The standard NCI methodology which was employed is described in Michael R Boyd, Principles and Practices of Oncology, Vol, 3, No. 10 (October 1989) and Monks A. et al., Journal of the National Cancer Institute, Vol. 83, No. 11, (Jun. 5, 1991).

The results of two separate screening experiementes carried out using uscharin are given in Tables 1 and 2.

The data are derived from Dose-Response Curves and two typical curves for leukemia and colon cancer are given for illustrative purposes in FIGS. 1 and 2 attached hereto.

The Dose-Response Curve is created by plotting the Calculated Percent Growth (PG) of each cell line against the $\log_{(10)}$ of the corresponding drug concentration. The cell line curves are grouped by cell type, or subpanel. Mean $\text{Log}_{(10)}$ concentrations for all cell lines tested are calculated at three points: where the test compound achieved 50% inhibition of cell growth ($GI_{50}$), where the test compound achieved 0% cell growth or total growth inhibition (TGI), and where the test compound achiveved 50% cell kill or 50% lethal concentration ($LC_{50}$). Reference lines are shown at the percent growth values of +50 ($GI_{50}$), 0 (TGI) and −50 ($LC_{50}$).

Percentage Growth (PG)—of the compound on a cell line is currently calculated according to one of the following expressions:

If (Mean $OD$(test)−Mean $OD$(tzero)>=0, then $PG=100\times$(Mean $OD$(test)−Mean $OD$(tzero)/(mean $OD$(ctrl)−Mean $OD$(tzero)

If (Mean $OD$(test−Mean $OD$(tzero)<0, then $PG=100\times$(Mean $OD$(test)−Mean $OD$(tzero)/Mean $OD$(tzero)

Where:
Mean OD (tzero)=The average of optical density measurements of SRB-derived colour just before exposure of cells to the test compound.
Mean OD (test)=The average of optical density measurements of SRB-derived colour after 48 hours with no exposure of cells to the test compound.
Mean OD (ctrl)=The average of optical density measurements of SRB-derived colour after 48 hours with no exposure of cells to the test compound.

It is clear from the results given in Tables 1 and 2 that uscharin has an inhibitory effect on the growth of a wide variety of cancer cell lines in vitro.

EXAMPLE 5
In vitro Screening of Uscharidin

Uscharidin was also subjected to in vitro cell screening in the manner described in Example 4. Results are given in Table 3 and FIG. 3, and these show that Uscharidin also exerts an inhibitory effect on a variety of cancer cell lines in vitro.

EXAMPLE 6
In vitro Screening of Calotoxin

Calotoxin was also subjected to in vitro cell screening in the manner described in Example 4. Results are given in Table 4 and FIG. 4, which show that calotoxin also exerts an inhibitory effect on a variety of cancer cell lines in vitro.

EXAMPLE 7
In vitro Experiement with Uscharin in Nude Mice

The SCCI cells (human tumour cell line) where grown ($1\times10^5$/ml seeding density) in 25 ml RPMI 1640 (10% foetal calf serum, 5% glutamine) in 75 $cm^2$ tissue culture flasks. The cells were harvested at log growth phase (5 days approximately) and washed once in saline before injection into the mice.

The "nude" mice (BALB/c nude) are reared and contained within a sealed isolator. The mice were injected with $1\times10^7$ cells subcut on the back, right hand side near the shoulder blades. After 7 days the mice were split randomly into the study groups (10–15 animals per group). Each was then treated with a different regime, the variable being time between injections and dose of drug at each injection, control groups were also included in the overall plan of the experiement.

During the trial a daily check was made on the animals and any animal removed if the tumour size became too large (>5–7% total body weight) or if the animal is showing signs of distress. Additional to this the tumour should be assessed every 3–4 days by an independent observer and the result recorded. Once an animal is removed from the study the tumour size, volume and weight was determined and the tumour stored for further cytological study. The reason for the animals removal from the study was also recorded, if this was not due to tumour size. The results are shown in the following tables.

Using nude mice injected with $10^7$ SCC-1 cells injected on day 0 and drug treatment started on day 9.

GROUP NO. 1
0.1 mg CGE-1/ Animal/ 5 days

| | | TUMOUR | | | | |
|---|---|---|---|---|---|---|
| MOUSE | DAY REMOVED | VOL. (mm³) | WEIGHT (g) | RATE (mg/D) | NECROTIC (%) | REASON |
| A | 27 | 4356.4 | 1.7492 | 64.8 | 22.41 | 1 |
| B | 55 | — | NONE | — | — | 5 |
| C | 30 | 4141.3 | 2.5658 | 85.5 | 45.28 | 1 |
| D | 30 | 299.8 | 1.8196 | 60.7 | 52.24 | 1 |
| E | 37 | 2752.8 | 1.5783 | 42.7 | 33.37 | 1 |
| F | 55 | — | NONE | — | — | 5 |
| G | 55 | — | NONE | — | — | 5 |
| H | 55 | — | NONE | — | — | 5 |
| I | 33 | 3414.9 | 1.8805 | 57.0 | 28.69 | 1 |
| J | 55 | — | NONE | — | — | 5 |
| K | 37 | 828.9 | 0.6773 | 18.3 | 8.19 | 2 |
| L | 27 | 2223.8 | 1.6854 | 62.4 | 48.92 | 1 |
| M | 27 | 1556.2 | 0.7728 | 28.6 | 5.45 | 1 |
| N | 27 | 3457.9 | 1.9394 | 71.8 | 52.94 | 1 |
| O | 55 | — | NONE | — | — | 5 |
| MEAN | | 2559.11 | 1.6298 | 54.64 | 33.05 | |
| S.D. | | 1437.34 | 0.5844 | 21.20 | 15.29 | |

GROUP NO. 2
0.1 mg CGE-1/ Animal/ 10 days

| | | TUMOUR | | | | |
|---|---|---|---|---|---|---|
| MOUSE | DAY REMOVED | VOL. (mm³) | WEIGHT (g) | RATE (mg/D) | NECROTIC (%) | REASON |
| A | 27 | 2993.1 | 2.0570 | 76.2 | 49.92 | 1 |
| B | 55 | — | NONE | — | — | 5 |
| C | 55 | — | NONE | — | — | 5 |
| D | 55 | — | NONE | — | — | 5 |
| E | 55 | 664.8 | 0.4333 | 7.9 | 17.91 | 5 |
| F | 55 | 3148.8 | 2.0378 | 37.1 | 16.96 | 5 |
| G | 55 | 134.4 | 0.1285 | 2.3 | 8.17 | 5 |
| H | 55 | — | NONE | — | — | 5 |
| I | 55 | — | NONE | — | — | 5 |
| J | 55 | — | NONE | — | — | 5 |
| K | 55 | — | NONE | — | — | 5 |
| L | 55 | — | NONE | — | — | 5 |
| M | 26 | 2025.9 | 1.3238 | 50.9 | 6.90 | 3 |
| N | 30 | 1548.8 | 1.2677 | 42.3 | 10.79 | 1 |
| O | 30 | 544.1 | 0.3827 | 12.8 | 25.29 | 4 |
| MEAN | | 1579.99 | 1.0901 | 32.79 | 19.42 | |
| S.D. | | 1201.27 | 0.7933 | 26.68 | 14.9 | |

GROUP NO. 3
0.5 mg CGE-1/ Animal/ 5 days

| | | TUMOUR | | | | |
|---|---|---|---|---|---|---|
| MOUSE | DAY REMOVED | VOL. (mm³) | WEIGHT (g) | RATE (mg/D) | NECROTIC (%) | REASON |
| A | 55 | — | NONE | — | — | 5 |
| B | 55 | 219.6 | 0.2082 | 3.8 | 18.18 | 5 |
| C | 55 | — | NONE | — | — | 5 |
| D | 19 | 1494.7 | 1.1889 | 62.6 | 2.33 | 3 |

-continued

GROUP NO. 3
0.5 mg CGE-1/ Animal/ 5 days

| MOUSE | DAY REMOVED | TUMOUR VOL. (mm³) | WEIGHT (g) | RATE (mg/D) | NECROTIC (%) | REASON |
|---|---|---|---|---|---|---|
|   | 19 | 203.2 | 0.0948 | 5.0 | — |   |
| E | 19 | — | NONE | — | — | 3 |
| F | 23 | 3912.0 | 2.5341 | 110.2 | 13.13 | 1 |
| G | 28 | 4463.2 | 2.5717 | 91.8 | 23.42 | 1 |
| H | 37 | — | NONE | — | — | 2 |
| I | 28 | 1666.5 | 1.0930 | 39.0 | 12.96 | 1 |
| J | 19 | 23.7 | 0.0038 | 0.2 | — | 3 |
| K | 33 | 1457.9 | 1.2546 | 38.0 | 19.22 | 1 |
| L | 29 | 1532.5 | 0.8926 | 30.8 | 12.49 | 1 |
| M | 29 | 2972.3 | 1.6348 | 56.4 | 17.79 | 1 |
| N | 37 | 537.9 | 0.4997 | 13.5 | 9.70 | 2 |
| O | 37 | — | NONE | — | — | 2 |
| MEAN |   | 1848.36 | 1.1976 | 45.12 | 14.36 |   |
| S.D. |   | 1504.32 | 0.8738 | 36.61 | 6.18 |   |

GROUP NO. 4
0.5 mg CGE-1/ Animal/ 10 days

| MOUSE | DAY REMOVED | TUMOUR VOL. (mm³) | WEIGHT (g) | RATE (mg/D) | NECROTIC (%) | REASON |
|---|---|---|---|---|---|---|
| A | 28 | 1482.1 | 1.1211 | 40.0 | 28.48 | 1 |
| B | 27 | 3499.1 | 2.5087 | 92.9 | 32.54 | 1 |
| C | 42 | 1930.3 | 1.4088 | 33.5 | 13.58 | 1 |
| D | 42 | 2177.3 | 1.5067 | 35.9 | 17.14 | 1 |
| E | 55 | — | NONE | — | — | 5 |
| F | 27 | 6682.3 | 3.1626 | 117.1 | 42.37 | 1 |
| G | 33 | 760.9 | 0.7467 | 22.6 | 50.31 | 1 |
| H | 55 | — | NONE | — | — | 5 |
| I | 55 | — | NONE | — | — | 5 |
| J | 55 | — | NONE | — | — | 5 |
| K | 55 | 64.5 | 0.1127 | 2.0 | 17.78 | 5 |
| L | 29 | — | NONE | — | — | 2 |
| M | 55 | — | NONE | — | — | 5 |
| N | 23 | 4929.6 | 2.6126 | 113.6 | 37.52 | 1 |
| O | 55 | — | NONE | — | — | 5 |
| MEAN |   | 2715.76 | 1.6475 | 57.2 | 29.97 |   |
| S.D. |   | 2272.64 | 1.0344 | 44.08 | 13.18 |   |

GROUP NO. 5
CONTROL (0.1 ml Saline/ Animal/ 5 days

| MOUSE | DAY REMOVED | TUMOUR VOL. (mm³) | WEIGHT (g) | RATE (mg/D) | NECROTIC (%) | REASON |
|---|---|---|---|---|---|---|
| A | 55 | — | NONE | — | — | 5 |
| B | 55 | — | NONE | — | — | 5 |
| C | 55 | — | NONE | — | — | 5 |
| D | 55 | — | NONE | — | — | 5 |
| E | 23 | 4570.9 | 2.4227 | 105.3 | 35.2 | 1 |
| F | 50 | 3138.3 | 1.9475 | 39.0 | 4.43 | 1 |
| G | 55 | — | NONE | — | — | 5 |

GROUP NO. 5
CONTROL (0.1 ml Saline/ Animal/ 5 days)

| MOUSE | DAY REMOVED | VOL. (mm³) | WEIGHT (g) | RATE (mg/D) | NECROTIC (%) | REASON |
|---|---|---|---|---|---|---|
| H | 55 | — | NONE | — | — | 5 |
| I | 3 | — | NONE | — | — | 3 |
| J | 23 | 5493.0 | 3.1602 | 137.4 | 59.07 | 1 |
| K | 28 | 2500.7 | 1.8958 | 67.7 | 6.68 | 1 |
| L | 28 | 3246.9 | 1.9716 | 70.4 | 31.86 | 1 |
| M | 55 | — | NONE | — | — | 5 |
| N | 28 | 4120.3 | 2.2965 | 82.0 | 46.07 | 1 |
| O | 55 | — | NONE | — | — | 5 |
| MEAN | | 3845.02 | 2.2707 | 83.63 | 30.55 | |
| S.D. | | 1093.88 | 0.4797 | 34.01 | 21.59 | |

Notes

Reasons (1) Removed due to tumour size.

(2) Removed due to another illness.

(3) Found dead in cage.

(4) Removed because the tumour was about to rupture.

(5) Removed at end of the experiment.

TABLE 5

Table 5 gives a summary of the results.

| | Tumour growth (mg/day) | % Necrosis* | % Mortality at 40 days |
|---|---|---|---|
| Group 1 (0.1 mg/5 days) | 54.6 ± 21.1 | 33.1 ± 18.3 | 84 |
| Group 2 (0.1 mg/10 days) | 32.8 ± 26.7 | 19.4 ± 14.9 | 55 |
| Group 3 (0.5 mg/5 days) | 45.1 ± 36.6 | 14.4 ± 6.2 | 90 |
| Group 4 (0.5 mg/10 days) | 57.2 ± 44.1 | 30.0 ± 13.2 | |
| Control | 83.6 ± 34.0 | 30.6 ± 21.6 | 100 |

*from histological examination
Values are means ±SD, n = 15

From these results it can be seen that a reduction in percentage mortallity due to the cancer cells of up to 45% can be achieved by administration of the compound of the invention (Uscharin).

What is claimed is:

1. A method of treatment of cell proliferation sensitive to isolated or synthesised uscharin or salts thereof in a human or non-human animal body, said method comprising administering to said body a composition comprising an effective amount of isolated or synthesised uscharin or salts thereof.

2. A method as claimed in claim 1 wherein a unit dose of composition comprises between 20 and 500 mg uscharin.

* * * * *